(12) United States Patent
Wong et al.

(10) Patent No.: US 10,959,766 B2
(45) Date of Patent: Mar. 30, 2021

(54) WIRE TENSIONER TIP

(71) Applicant: Wright Medical Technology, Inc., Memphis, TN (US)

(72) Inventors: Kian-Ming Wong, Lakeland, TN (US); Freddie Lobianco, Millington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 121 days.

(21) Appl. No.: 16/152,650

(22) Filed: Oct. 5, 2018

(65) Prior Publication Data

US 2019/0119064 A1    Apr. 25, 2019

Related U.S. Application Data

(60) Provisional application No. 62/576,872, filed on Oct. 25, 2017.

(51) Int. Cl.
| | | |
|---|---|---|
| *A61B 17/88* | (2006.01) | |
| *A61B 17/62* | (2006.01) | |
| *A61B 17/66* | (2006.01) | |

(52) U.S. Cl.
CPC .......... *A61B 17/8869* (2013.01); *A61B 17/62* (2013.01); *A61B 17/66* (2013.01)

(58) Field of Classification Search
CPC ...... A61B 17/8869; A61B 17/62; A61B 17/66
USPC .............................................. 606/56–59, 103
See application file for complete search history.

(56) References Cited

U.S. PATENT DOCUMENTS

| | | | |
|---|---|---|---|
| 2,291,413 A * | 7/1942 | Siebrandt ........... | A61B 17/8861 606/103 |
| 5,057,113 A | 10/1991 | Mingozzi | |
| 5,431,659 A | 7/1995 | Ross, Jr. et al. | |
| 6,443,955 B1 * | 9/2002 | Ahrend .............. | A61B 17/8866 606/103 |
| 8,333,766 B2 * | 12/2012 | Edelhauser ............ | A61B 17/62 606/55 |
| 8,617,185 B2 * | 12/2013 | Bonutti .............. | A61B 17/8869 606/144 |
| 9,757,153 B2 * | 9/2017 | Jay ........................ | A61B 17/62 |

(Continued)

FOREIGN PATENT DOCUMENTS

| | | |
|---|---|---|
| SU | 594974 A | 2/1978 |
| WO | 1991006253 A1 | 5/1991 |

(Continued)

OTHER PUBLICATIONS

Office Action issued in connection with Canadian Patent Application No. 3,020,973, 4 pages, dated Nov. 13, 2019.

(Continued)

*Primary Examiner* — Eduardo C Robert
*Assistant Examiner* — David C Comstock
(74) *Attorney, Agent, or Firm* — Duane Morris LLP

(57) ABSTRACT

A wire tensioner tip includes a body having a first extension and a second extension spaced apart to define a ring slot. An engagement body is disposed within the ring receiving slot. The engagement body includes one or more projections configured to engage an outer surface of a ring positioned within the ring receiving slot. A coupling element extends from the body and is configured to couple the body to a wire tensioner.

18 Claims, 38 Drawing Sheets

(56) References Cited

U.S. PATENT DOCUMENTS

2014/0155906 A1* 6/2014 Pratt .................. A61B 17/8869
   606/103
2016/0066956 A1   3/2016 Siemer et al.

FOREIGN PATENT DOCUMENTS

| WO | 1995005127 A2 | 2/1995 |
| WO | 2015167581 A1 | 11/2015 |
| WO | 2016094636 A1 | 6/2016 |

OTHER PUBLICATIONS

Extended European Search Report issued in connection with European Patent Application No. 18201912, 7 pages, dated Mar. 4, 2019.
First Examination Report issued in connection with Australian Patent Application No. 2018247285, 10 pages, dated May 6, 2019.
Office Action issued in connection with the Canadian Patent Application No. 3,020,973, 4 pages, dated Jun. 23, 2020.
First Examination issued in connection with Australian Patent Application No. 2020200558, 12 pages, dated May 22, 2020.

* cited by examiner

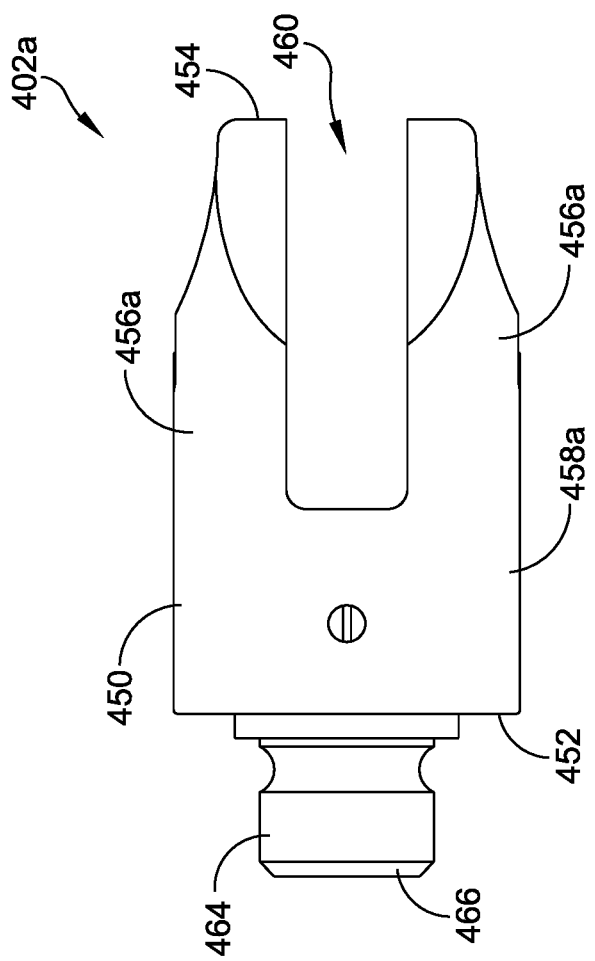

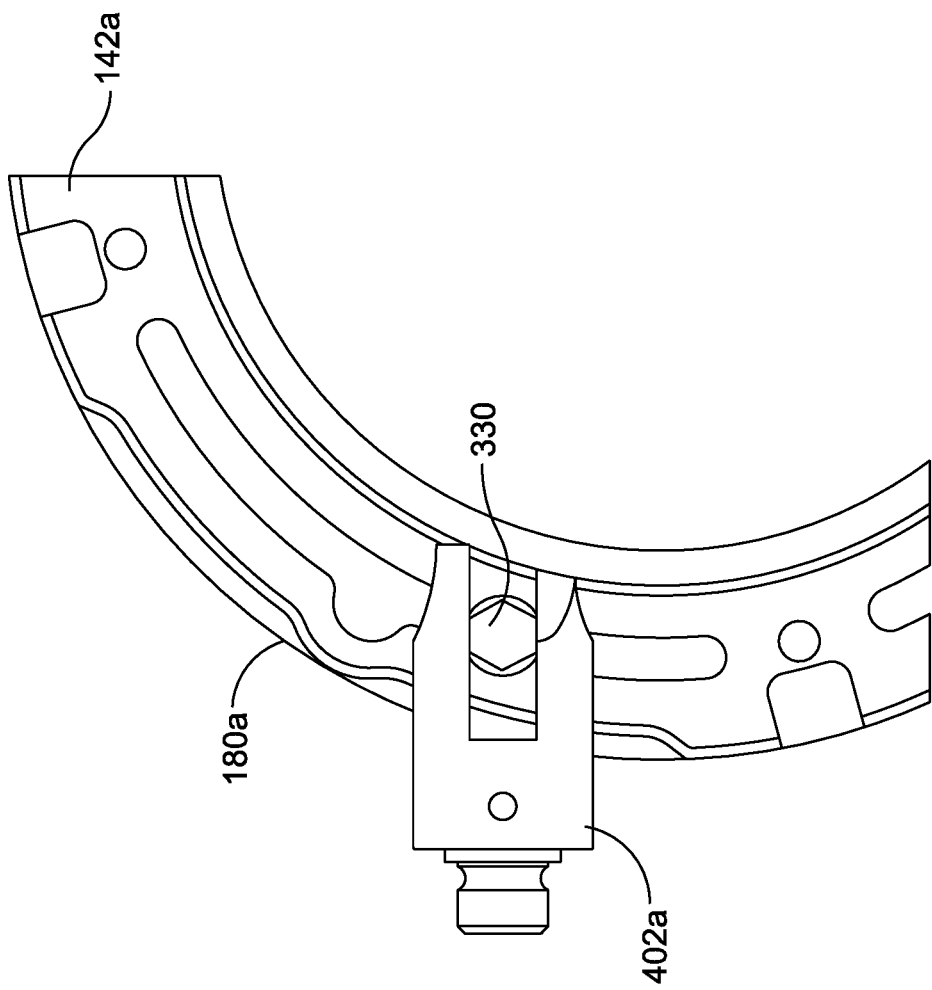

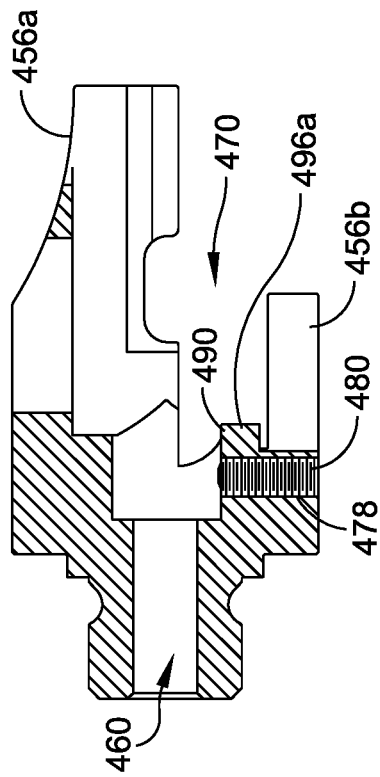
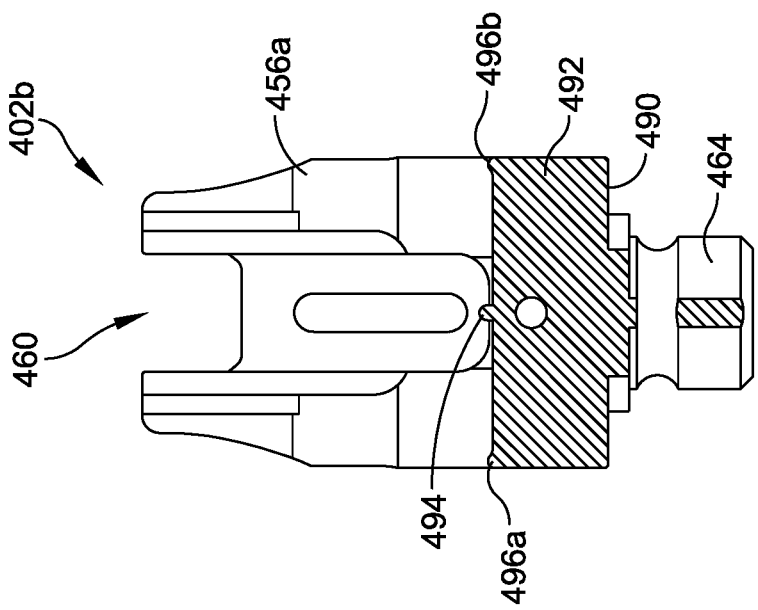

WIRE TENSIONER TIP

CROSS-REFERENCE TO RELATED APPLICATION

This application claims benefit to U.S. Provisional Application Ser. No. 62/576,872, filed Oct. 25, 2017, entitled "WIRE TENSIONER TIP," and which is incorporated by reference herein in its entirety.

BACKGROUND

For most standard arthrodesis (i.e., circular frame) procedures, a prebuilt frame including two tibial rings and a foot plate with an extension can be utilized. A circular fixator system can be used for open or closed fracture fixation, pseudoarthrosis or nonunions of long bones, limb lengthening by epiphyseal or metaphyseal distraction, correction of bony or soft tissue deformities, or correction of segmental or nonsegmental bony or soft tissue defects. Circular Fixators have been used on long bones including: the tibia, fibula, femur, humerus, radius, and ulna.

Prior to insertion of wires or pins, the circular fixator is positioned around the tibia and foot. The leg is eccentrically located in the frame to accommodate the posterior musculature, and the plantar aspect of the foot extends above or below the foot plate. To maintain the tibia and foot in position, folded up towels can be placed under the calf. The surgeon inserts wires through the bones, and secures the wires to the frame. Current systems use bolts that are inserted into holes in the rings and foot plate of the frame.

SUMMARY

In various embodiments, a wire tensioner tip is disclosed. The wire tensioner tip includes a body having a first extension and a second extension spaced apart to define a ring slot, an engagement body disposed within the ring receiving slot, and a coupling element extending from the body and configured to couple the body to a wire tensioner. The engagement body includes one or more projections configured to engage an outer surface of a ring positioned within the ring receiving slot.

In various embodiments, a wire tensioner is disclosed. The wire tensioner includes a tensioning body comprising a handle portion and a tensioner and a tensioner tip coupled to the tensioning body. The handle portion includes a first handle and a second handle configured to actuate the tensioner. The tensioner is configured to apply a force to a wire inserted into the tensioner. The tensioner tip includes a tip body having a first extension and a second extension spaced apart to define a ring slot and an engagement body disposed within the ring receiving slot. The engagement body includes one or more projections configured to engage an outer surface of a ring positioned within the ring receiving slot.

In various embodiments, a system is disclosed. The system includes a circular fixator comprising at least one ring defining a slot, a wire fixation element sized and configured to be positioned within the slot of the circular fixator, and a wire tensioner. The wire tensioner includes a tensioning body comprising a handle portion and a tensioner and a tensioner tip coupled to the tensioning body. The handle portion includes a first handle and a second handle configured to actuate the tensioner. The tensioner is configured to apply a force to a wire inserted into the tensioner. The tensioner tip includes a tip body having a first extension and a second extension spaced apart to define a ring slot sized and configured to receive the at least one ring and an engagement body disposed within the ring receiving slot. The engagement body includes one or more projections configured to engage an outer surface of the at least one ring when the at least one ring is positioned within the ring slot.

In various embodiments, a method is disclosed. The method includes coupling a wire to a first fastener and a second fastener. The wire extends through at least a first bone. Each of the first fastener and the second fastener are coupled to a ring of a circular fixator. The first fastener is tightened to lock a first end of the wire in a fixed position and a wire tensioner is coupled to a second end of the wire. The wire tensioner includes a tensioning body including a tensioner defining a channel sized and configured to receive the wire therethrough and a tensioner tip coupled to the tensioning body. The tensioner tip includes a tip body having a first extension and a second extension spaced apart to define a ring slot sized and configured to receive the ring therein and an engagement body disposed within the ring receiving slot. The engagement body includes one or more projections configured to engage an outer surface of the ring when the ring is positioned within the ring slot. The wire is tensioned by the tensioner which is configured to apply a tensioning force to the wire. The second fastener is tightened to lock the second end of the wire in a fixed position.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 7A is a plan view of a wire tensioner tip configured to be coupled to the wire tensioner of FIG. 6, in accordance with some embodiments.

FIG. 11 is a plan view of the wire tensioner tip of FIG. 7A coupled to a ring of a circular fixator in an angled engagement, in accordance with some embodiments.

FIG. 14F is a cross-section of the wire tensioner tip taken along line F-F in FIG. 14C, in accordance with some embodiments.

FIG. 14G is a cross-section of the wire tensioner tip taken along line G-G in FIG. 14B, in accordance with some embodiments.

DETAILED DESCRIPTION

Figure 1A:
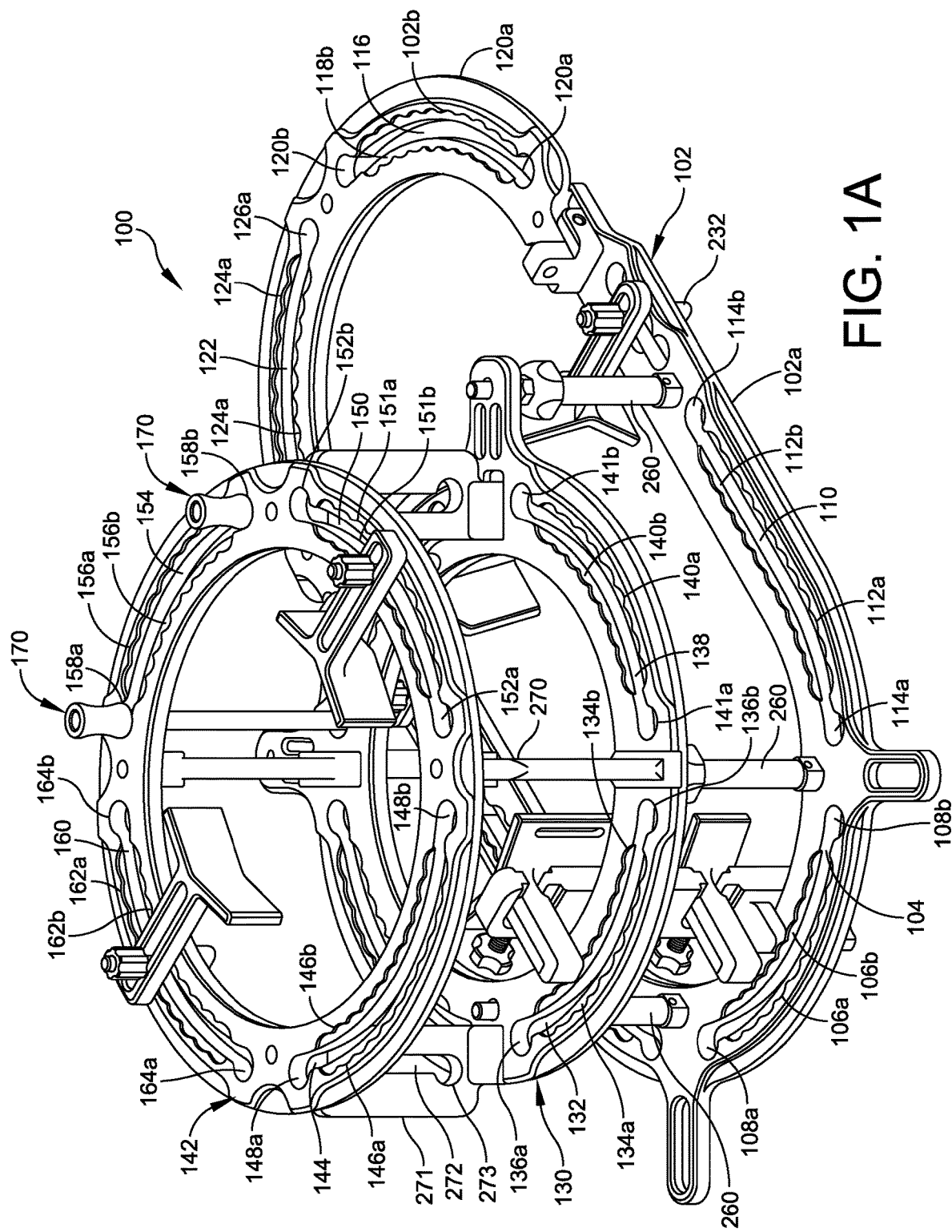
FIG. 1A is an isometric view of a circular fixator, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a wire tensioner including a wire tensioner tip is disclosed. The wire tensioner is configured to apply tension to a wire coupled to a circular fixator. The wire is inserted through the wire tensioner tip and the wire tensioner. The wire tensioner tip can include an engagement body configured to abut an outer surface of a ring of a circular fixator to maintain the wire tensioner in a fixed position during tensioning. The wire tensioner tip can include a pivoting and/or a fixed engagement body. The wire tensioner tip can include one or more projections configured to engage an outer surface of the ring and prevent movement, such as sliding and angulation, of the wire tensioner during tensioning.

Figure 1B:
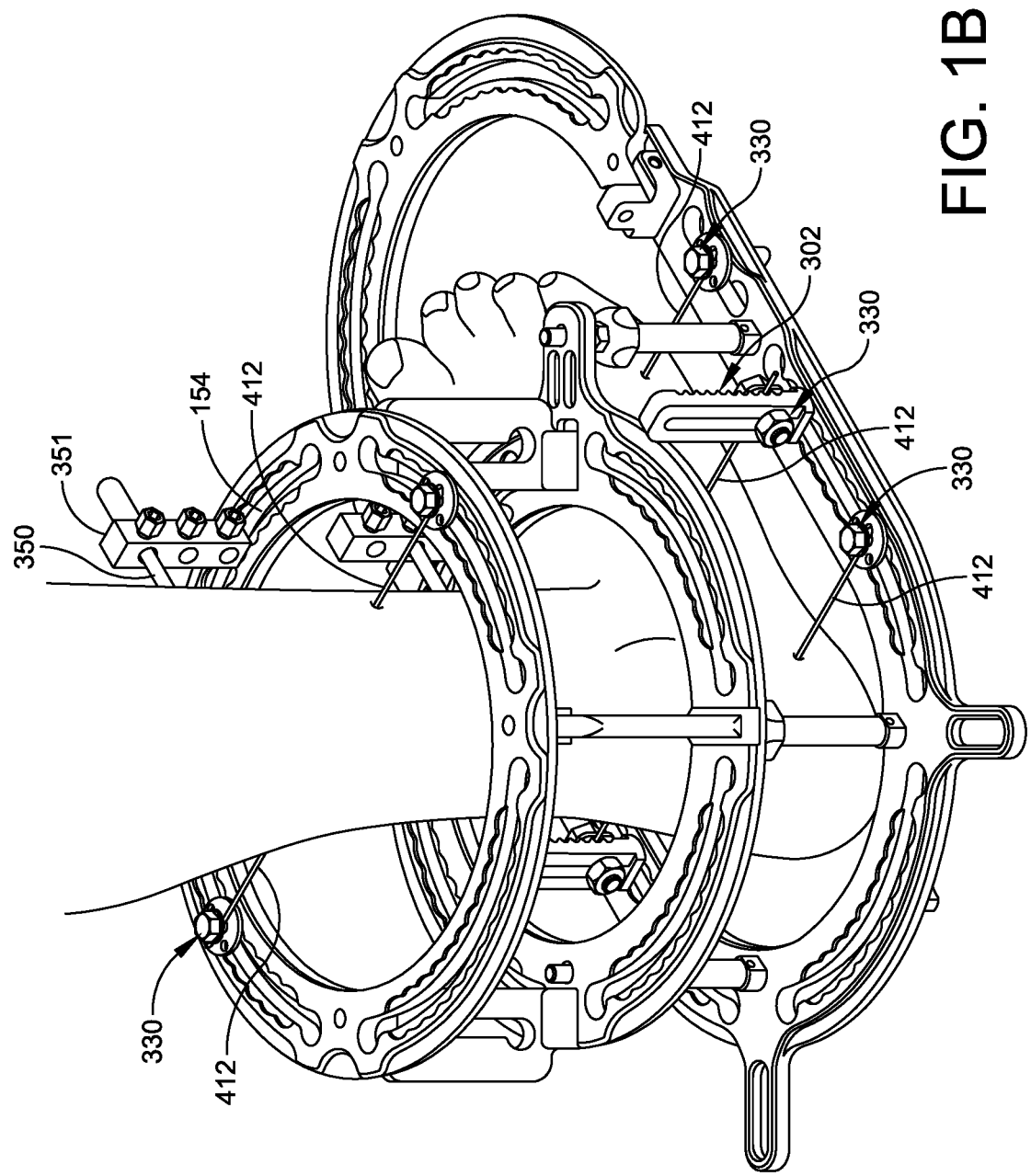
FIG. 1B illustrates a patient's leg fixed within the circular fixator of FIG. 1A, in accordance with some embodiments.
Figure 2:
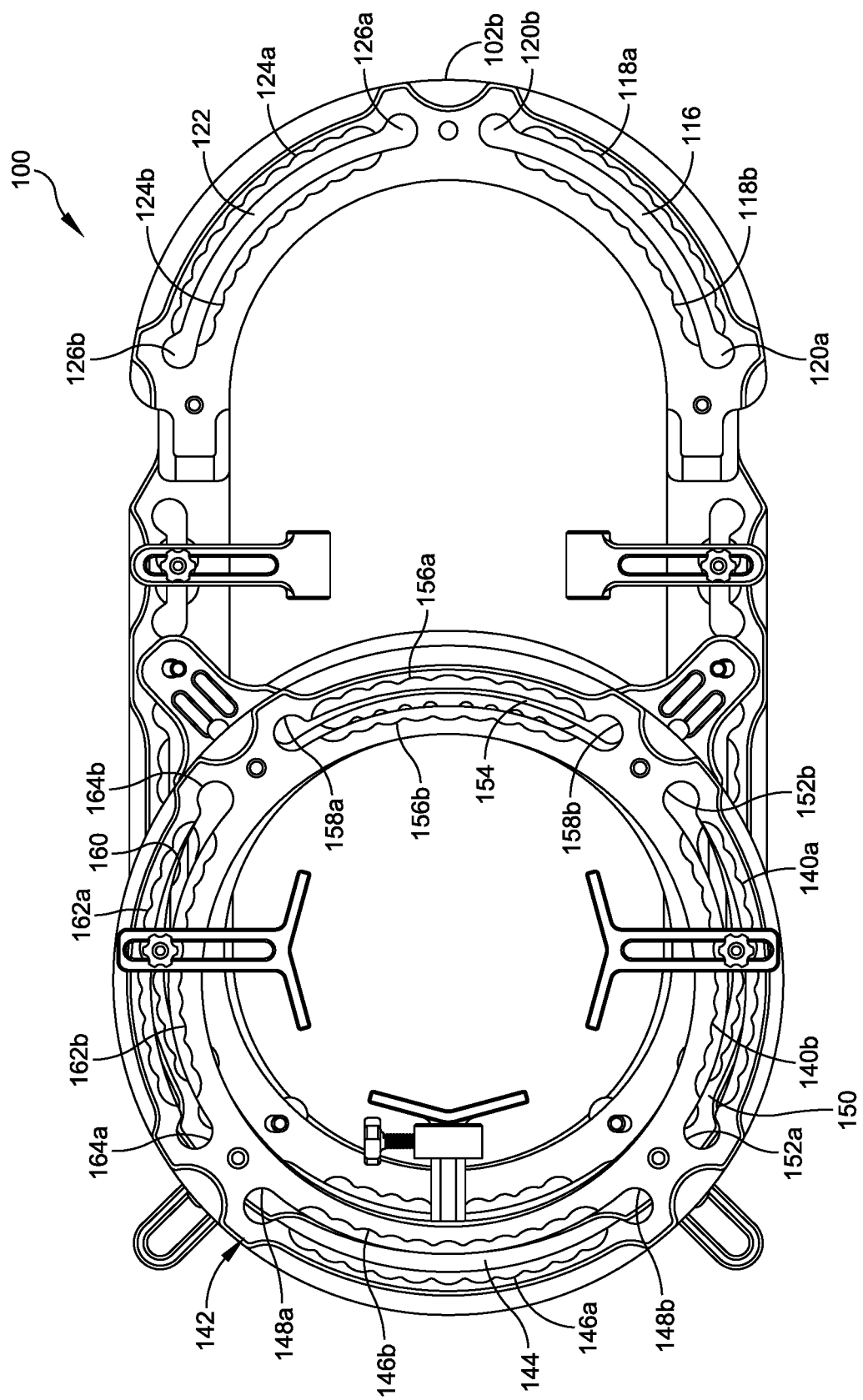
FIG. 2 is a plan view of the circular fixator of FIG. 1A, in accordance with some embodiments.
Figure 3:
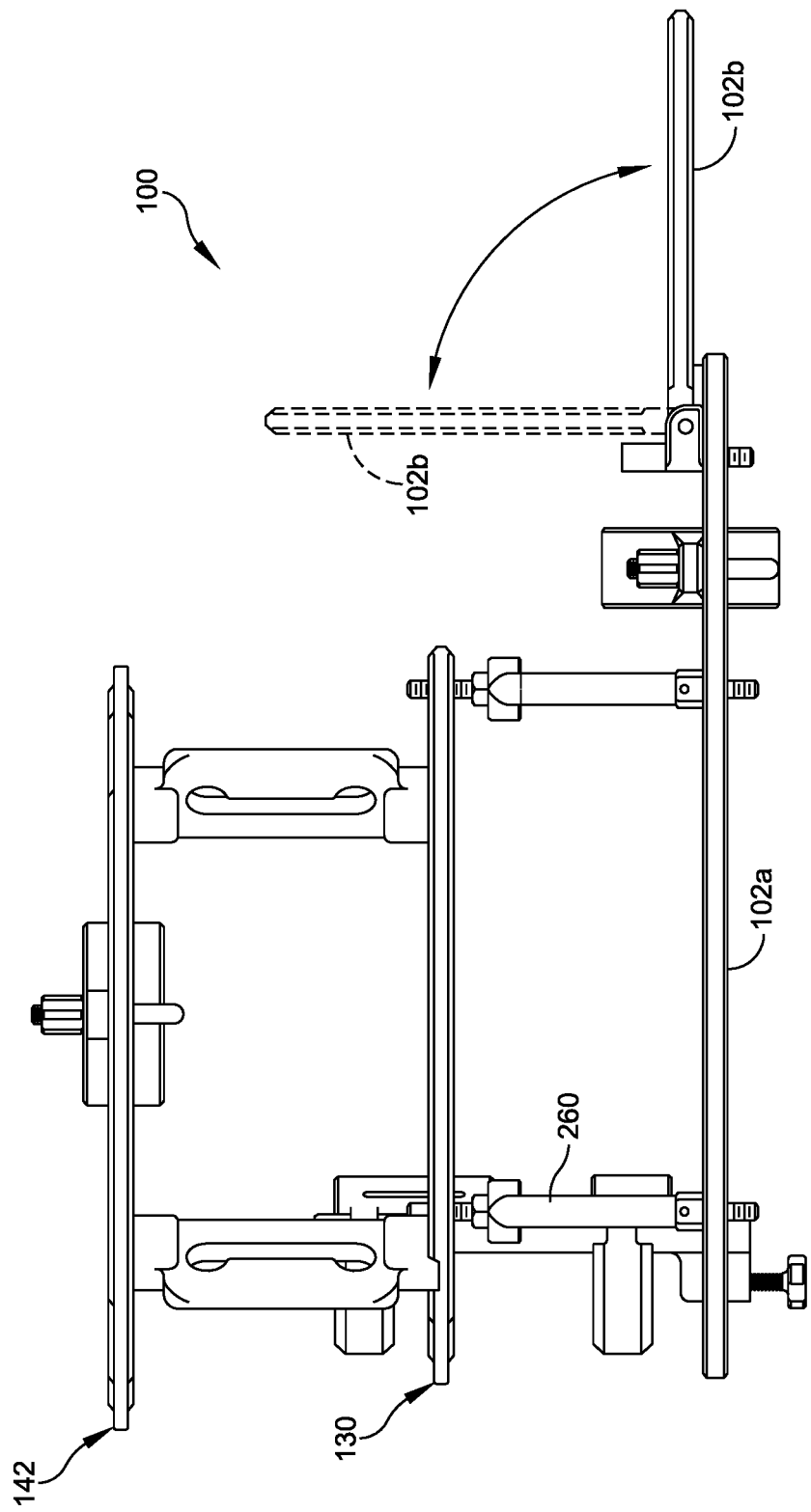
FIG. 3 is a posterior side elevation view of the circular fixator of FIG. 1A, in accordance with some embodiments.

FIG. 1A is an isometric view of a circular fixator 100 according to some embodiments of this disclosure. FIG. 1B shows the circulator fixator 100 with the patient's foot fixed by wires 412, following the procedures. FIGS. 2 and 3 show plan and side elevation views of the circular fixator 100.

The circular fixator 100 is a device comprising a plurality of rings 102, 130 and 142. In some embodiments, one ring 102 of the plurality of rings is elongated. The elongated ring 102 has a proximal portion 102a and a distal portion 102b. The elongated ring 102 is configured so that the distal portion 102b can be rigidly attached to the first portion 102a in a first position parallel to or coplanar with the proximal portion 102a. As shown in phantom in FIG. 3 the distal portion 102b can be rigidly attached to the first portion 102a in a second position having a non-zero angle with respect to the proximal portion. In some embodiments, the non-zero angle is 90 degrees.

In some embodiments, the plurality of rings include first and second circular rings 142, 130 adapted to be positioned around a leg of a patient during fixation, and the first ring 142 is greater in diameter than the second ring 130 and 102. This configuration permits the surgeon to maintain a constant distance. As a general rule of thumb, the clearance between the inner diameter of each ring and the nearest leg tissue is about two fingers' breadth (e.g., about 3.7 cm to about 4 cm), at different heights along the patient's leg. Similarly, if the fixator is adapted for use on another extremity, a similar clearance between the inner diameter of each ring and the nearest tissue is used. Because the patient's calf is greater in diameter further from the ankle, the top ring 142 is correspondingly greater in inner diameter than the middle ring 130. Because the ring 130 is smaller, it reduces the moment arm for pins or wires. For example, in one embodiment, the top ring 142 has an inner diameter of about 18 cm, and the middle ring 130 has an inner diameter of about 16 cm. This is just one example, and any combination of ring sizes can be used to accommodate the geometry of any given patient's calf.

Each ring 102, 130 and 142 has a first (e.g., top) face, a second (e.g., bottom) face, and at least one slot. For example, ring 102 has slots 104, 110, 116, 122; ring 130 has four slots, including slots 132, 138; and ring 142 has slots 144, 150, 154, and 160. Each slot is defined by first and second interior edges of its respective ring 102, 130 and 142 on opposing sides of the slot. Each slot (e.g., 104) penetrates from the first face of the ring (e.g., 102) to the second face. The first (e.g., top) face of each ring (e.g., 102) has a first scallop-shaped recess (e.g., 106a) adjacent the slot 104 on the first edge and a second scallop-shaped recess (e.g., 106b) adjacent the slot 104 on the second edge. The slot 104 terminates at an opening 108a, 108b at each respective end of the slot. The openings 108a, 108b have a dimension that is substantially greater than a width of the slot 106. Similarly, in the example of FIG. 1, slot 110 has scallop-shaped recesses 112a, 112b and end openings 114a, 114b; slot 116 has recesses 118a, 118b and end openings 120a, 120b; slot 122 has recesses 124a, 124b and end openings 126a, 126b; slot 132 has recesses 134a, 134b and end openings 136a, 136b; slot 138 has recesses 140a, 140b and end openings 141a, 141b; slot 144 has recesses 146a, 146b and end openings 148a, 148b; slot 150 has recesses 151a, 151b and end openings 152a, 152b; and slot 160 has recesses 162a, 162b and end openings 164a, 164b.

In other embodiments, instead of a scallop-shaped recess 134a, 134b, 146a, 146b, one or more of the rings include recess pockets. In some embodiments the circular fixator includes at least one ring 102 having scallop shaped recesses 106a, 106b, 112a, 112b, 118a, 118b, and at least one ring having recess pockets. The rings without the scallops may permit the fixation device 300 to move toward the wire more quickly without any chance of becoming caught in a scallop. Additionally, the recesses without scallops allow the surgeon to fix the fixation device 300 anywhere along the length of the slots, and the surgeon is not limited to any discrete set of fixed locations. If a wire is run perpendicular to the slots, there is little chance that the fixation device 300 can slip in the slot. If the wires are to be run perpendicular or nearly perpendicular to the slots, the surgeon may prefer that the rings without scallops are used for ease of use. On the other hand, the greater the angle between the wires and the slots, the greater the benefit of the scallops, for preventing slippage.

The device further includes a plurality of posts 270 joining each one of the plurality of rings 130, 142 to an adjacent one of the plurality of rings. In some embodiments, the center ring 130 is connected to the top ring 142 by fixed posts 270, and the center ring 130 is connected to the bottom ring 102 by a plurality of calibrated struts 260. The calibrated struts permit accurate and even adjustments to the distance between the bottom ring 102 and the center ring 130 (e.g., for compression/distraction of the foot or height adjustments to the desired height). In some embodiments, all of the posts 270 are of the same fixed type. In some embodiments, as shown in FIG. 1A, one or more of the posts 270 can be replaced by suitably configured plates 271, threaded rods, spacers, or struts. For example, the plates 271 can each have a respective vertical slot 272. Each slot 272 has openings 273 at the top and bottom of the slot. The slots 272 can have the same width as the slots 112a, 112b, and the openings 273 can have the same size as the openings 114a, 114b. The slots 272 of the plates 271 can receive fixations elements 330, and the openings 273 can receive plugs 170, for pre-loading the fixation elements 330, in the manner described below. In other embodiments, any combination of posts 270, plates 271, rods, spacers and/or struts can be used.

In some embodiments, each scallop-shaped recess (e.g., 112a, 112b) comprises a plurality of curved arcs, and each curved arc subtends an angle in a range from about 10 degrees to 170 degrees. In some embodiments, the subtended angle is in a range from 30 degrees to 150 degrees. In some embodiments, the subtended angle is in a range from 30 degrees to 150 degrees. In some embodiments, the subtended angle is in a range from 60 degrees to about 120 degrees. In some embodiments, each scallop-shaped recess comprises a plurality of circular arcs, each circular arc subtending an angle of about 90 degrees. The arcs subtend an angle that is sufficiently large to resist slipping of any fixation device relative to the slot, particularly if any force component is applied to the fixation device 330 parallel to the direction of the slot (e.g., 110). In some embodiments, the rings 102, 130, 142 comprise a metal, such as aluminum or titanium.

Figure 4:
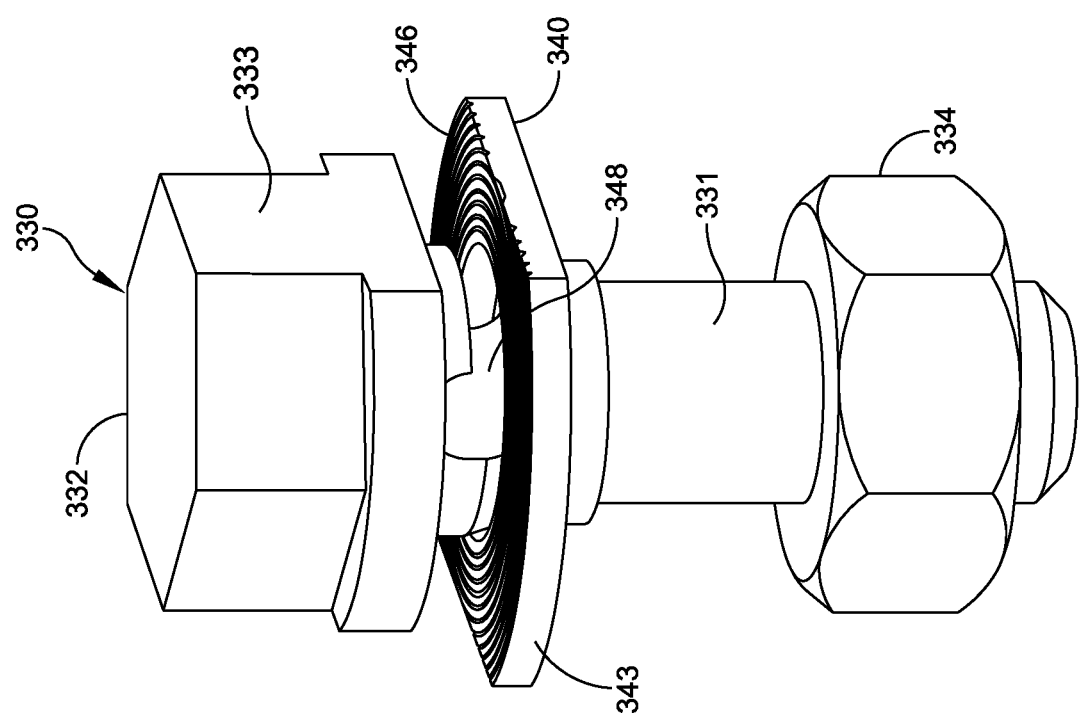
FIG. 4 is an isometric view of a fixation element configured to be coupled to the circular fixator of FIG. 1A, in accordance with some embodiments.
Figure 5:
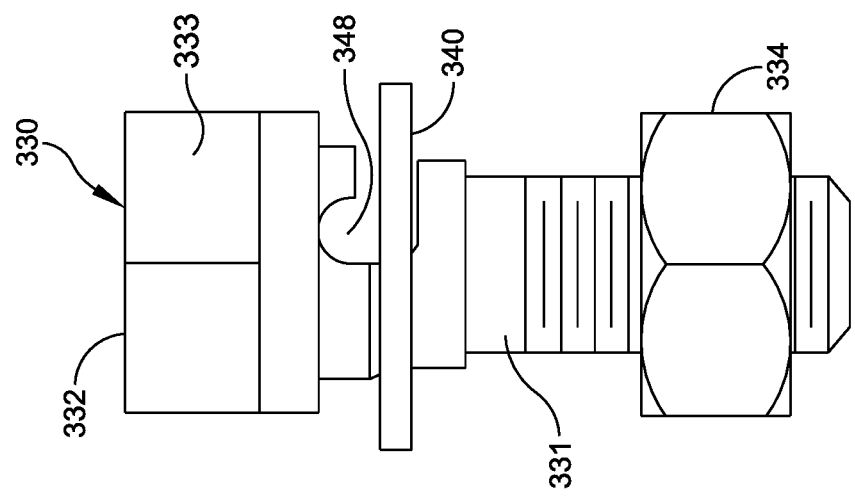
FIG. 5 is a side elevation view of the fixation element of FIG. 4, in accordance with some embodiments.

As shown in FIGS. 4-5, in some embodiments, at least one of the fixation devices 300 comprises a bolt 330, a nut 334 and a washer 340. The bolt 330 has head 332 and a threaded portion 331 sized to fit through the slot (e.g., 112a, 112b). The bolt 330 includes a side slot 348 in a side surface of the threaded portion 331, for receiving a wire 412. The washer 340 is shaped to fit a respective one of the curved arcs on the scallop-shaped recess 114a, 114b on each side of the slot 110 of the ring 102. In some embodiments, the washer 340 has a textured gripping surface 346 for securely positioning the wire. The washer 340 has two curved edges 343 adapted for fitting the curved arcs of the scallop shaped recesses. The remaining two edges of the washer can be flat. The gripping surface can have ridges, barbs, splines, slots, a knurled surface, or the like. In some embodiments, the opening (e.g., 114a, 114b) at each end of each slot (e.g., 112a, 112b) is adapted to receive a nut 334 of a fixation device 330 through the opening. In some embodiments, the slot (e.g., 112a, 112b) is adapted to receive a threaded portion 331 of the fixation device 330 through the slot, but the slot has a width that is smaller than a dimension of the nut 334. Thus, once the nut 334 is affixed to the threaded portion 331, the fixation device 330 can be inserted into the openings (e.g., 114a, 114b) but cannot fall out of the slots. The fixation devices can be pre-assembled, and the pre-assembled fixation devices can pre-loaded onto the slots prior to surgery. The openings (e.g., 114a, 114b) can be then be plugged to prevent release of the fixation devices 330.

Some embodiments further comprise at least one post having a threaded body portion adapted to fit through the slot (e.g., 110) of the ring 102. The post has a longitudinal slot through the post (and parallel to the longitudinal axis of the post) for receiving a bolt of the fixation device 300. In some embodiments, the surgeon can also insert rods into the bone using the circulator fixator 100. A pin cube 351 can be mounted in the slot (e.g., 154) for fixing the pin (also referred to as a rod). International Application Publication WO2015/167581, entitled "CIRCULAR FIXATOR SYSTEM AND METHOD," published on Nov. 5, 2015, is incorporated herein by reference in its entirety.

Figure 6:
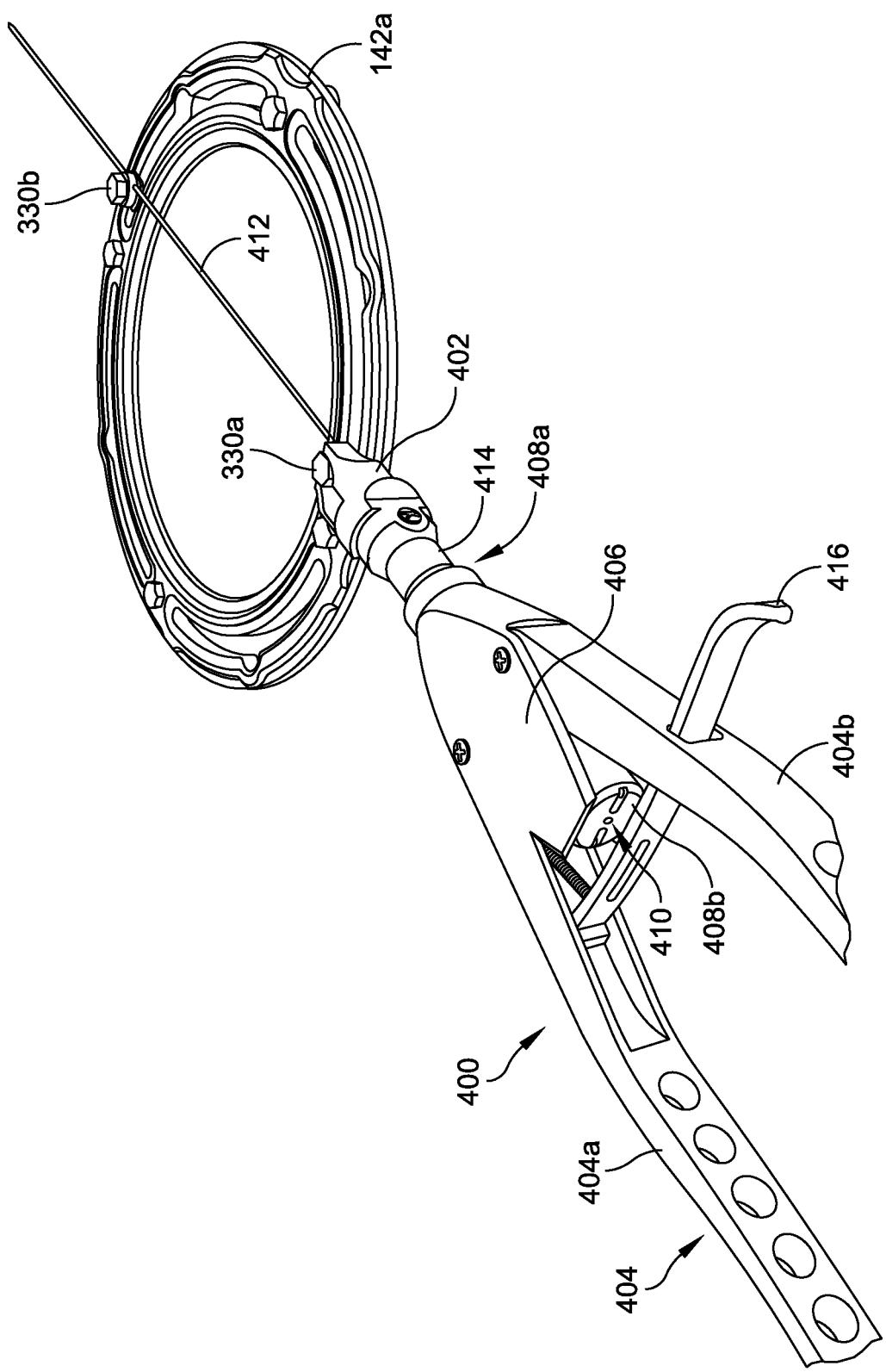
FIG. 6 is an isometric view of a wire tensioner coupled to a wire extending from a first a fixation element to a second fixation element, in accordance with some embodiments.
Figure 7C:
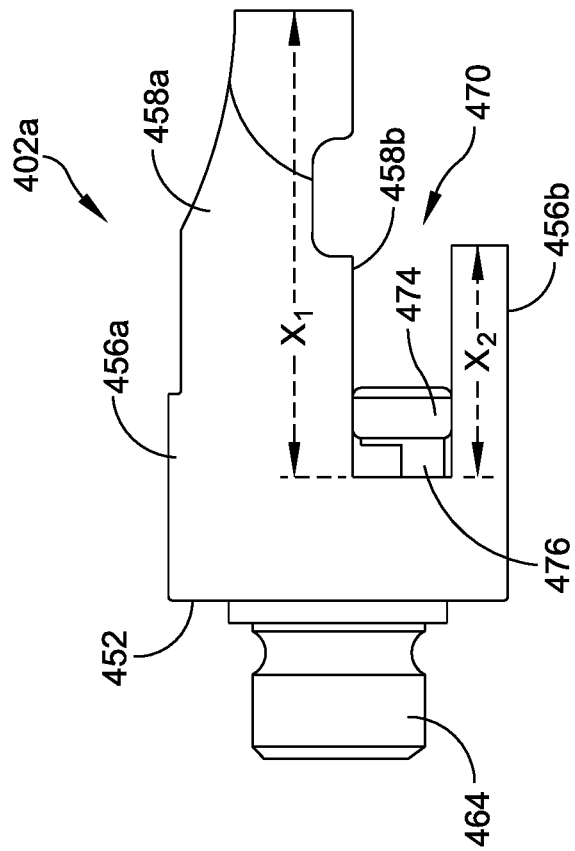
FIG. 7C is a side elevation view of the wire tensioner tip of FIG. 7A, in accordance with some embodiments.
Figure 7B:
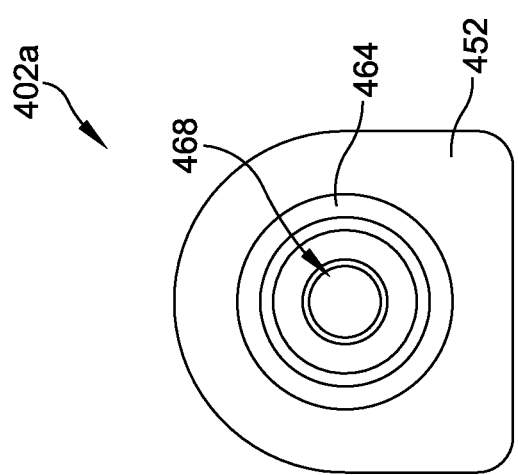
FIG. 7B is a posterior view of the wire tensioner tip of FIG. 7A, in accordance with some embodiments.
Figure 7E:
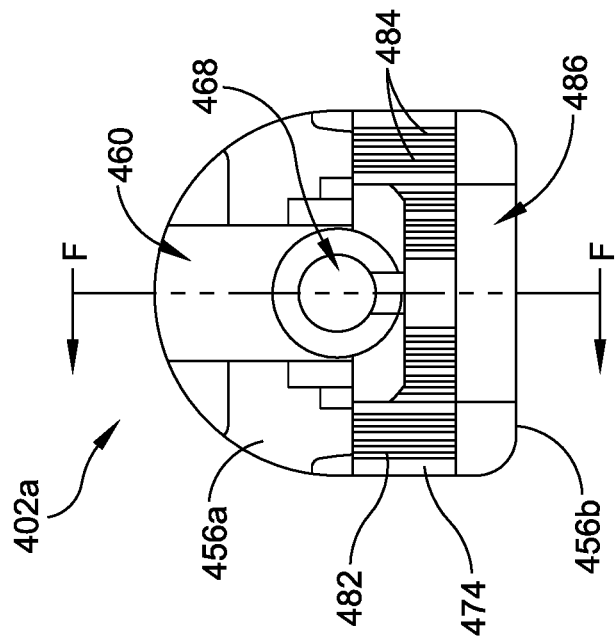
FIG. 7E is a front elevation view of the wire tensioner tip of FIG. 7A, in accordance with some embodiments.
Figure 7D:
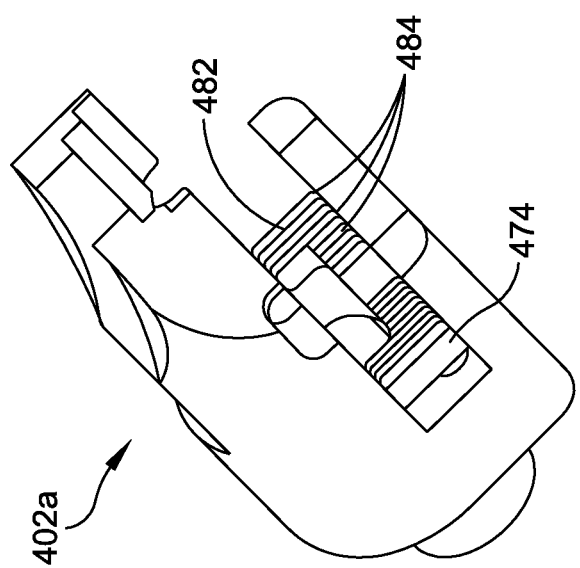
FIG. 7D is a front isometric view of the wire tensioner tip of FIG. 7A, in accordance with some embodiments.
Figure 7G:
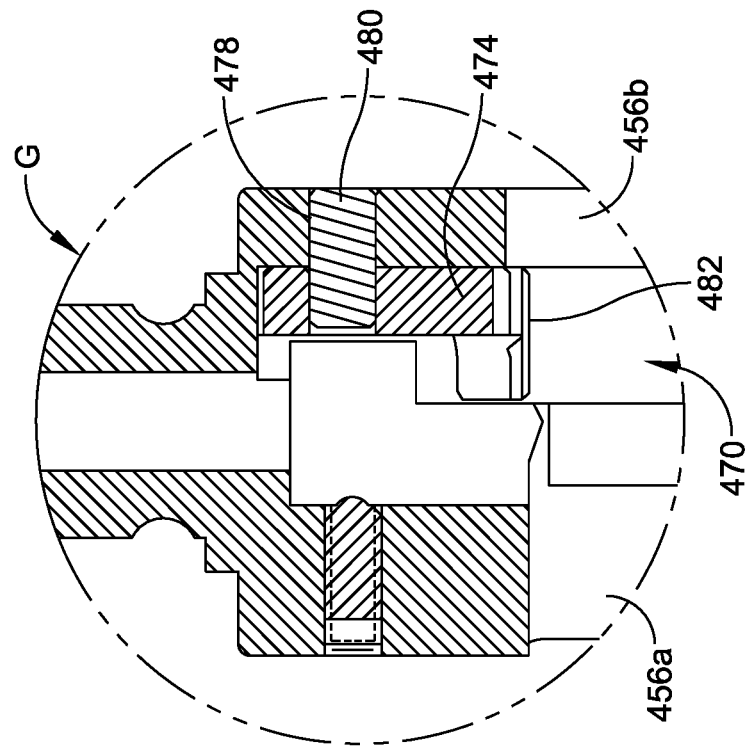
FIG. 7G is an enlarged view of area 'A' illustrated in FIG. 7F, in accordance with some embodiments.
Figure 7F:
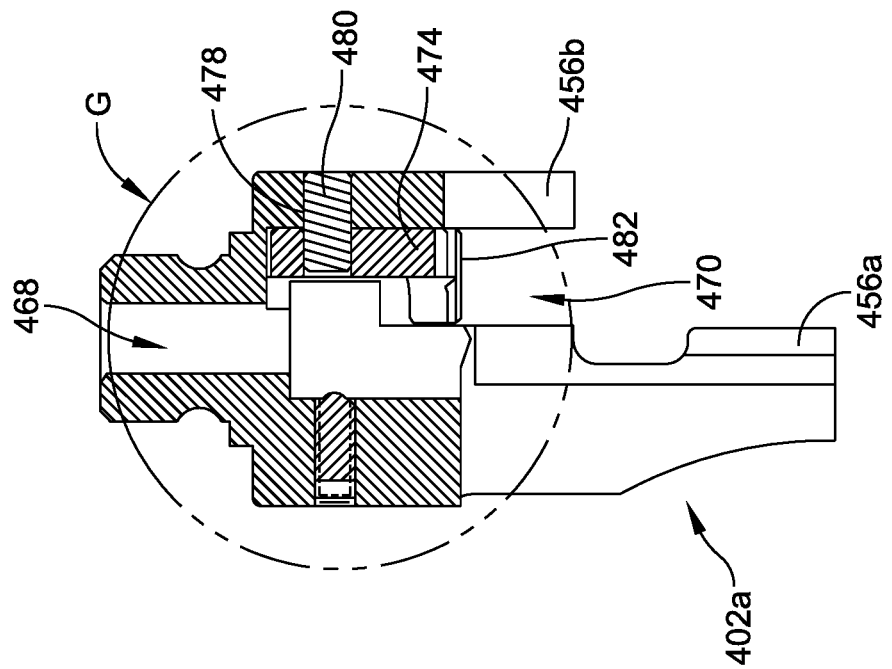
FIG. 7F is a cross-section of the wire tensioner tip taken along line F-F in FIG. 7E, in accordance with some embodiments.

After coupling a wire 412 to one or more fixation devices 300, the wire 412 can be tensioned to position one or more bones. As shown in FIG. 6, a wire tensioner 400 can be coupled to a wire 412 extending from a first fixation device 330a and/or a second fixation device 330b. The wire 412 extends through a side slot 348 of the fixation device 330a, 330b and can be loosely and/or firmly held by a washer 340. The wire 412 is inserted through an opening (see FIG. 7B) in a wire tensioner tip 402. In some embodiments, an actuation mechanism 406 of the wire tensioner 400 defines a wire slot 410 extending from a first end 408a to a second end 408b. The wire 412 extends at least partially into the wire slot 410.

A handle portion 404 includes a first handle 404a and a second handle 404b that can be squeezed (or otherwise actuated) to apply tension to the wire 412 extending through the wire tensioner tip 402. The handles 404a, 404b can be actuated to apply a predetermined amount of tension to the wire 412 corresponding to a selected movement and/or selected position of at least one bone. In some embodiments, the wire tensioner 400 can include an indicator 414 configured to provide a visual indication regarding the amount of tension applied to the wire 412. The wire tensioner 400 can include a locking bar 416 to lock the wire tensioner 400 at a selected tension.

In use, the wire tensioner 400 applies tension to a wire 412 after the wire 412 is passed through the patient. The wire 412 is initially coupled to a first fixation device 330a and/or a second fixation device 330b. One of the fixation devices, such as the second fixation device 330b, is tightened to anchor (or fix) a first end of the wire 412. The second fixation device, such as the first fixation device 330a, is partially tightened to maintain the wire 412 within the side slot 348 while still allowing some movement of the wire 412 within the side slot 348. The tensioner 400 is coupled to a second end of the wire 412 extending from the first fixation device 330a. A selected tension is applied to the wire 412 by the tensioner 400 and the first fixation device 330a is further tightened to fix the wire 412 at the selected tension. The tensioner 400 can be released from the wire 412 after tightening the first and/or second fixation devices 330a, 330b.

Although embodiments are illustrated and discussed herein including tensioning handles 404a, 404b, it will be appreciated that any suitable wire tensioner configured to receive a wire tensioner tip 402 can be used and is within the scope of this disclosure. For example, in some embodiments, a wire tensioner may include a cylinder configured to be coupled to a wire tensioner tip 402 and rotated to apply tension to a wire 412 inserted through the wire tensioner tip 402. In other embodiments, handles, rotatable cylinders, and/or any other suitable elements can be configured to apply tension to wire 412 inserted through a wire tensioning tip 402.

FIGS. 7A-7G illustrates a wire tensioner tip 402a configured to be coupled to a wire tensioner 400, in accordance with some embodiments. The wire tensioner tip 402a includes a body 450 extending from a proximal (or rear) surface 452 to a distal (or front) surface 454. The body 450 includes a first (or upper) extension 456a and a second (or lower) extension 456b. The first and second extensions 456a, 456b are spaced apart by a ring slot 470. In some embodiments, the first extension 456a includes a curved (or arced) outer surface 458a and a flat inner surface 458b. The flat inner surface 458b is configured to abut a first surface of a ring, such as ring 142. The second extension 456b includes a flat outer surface 460a and a spaced apart flat inner surface 460b. The flat inner surface 460b is configured to abut a second surface of a ring, such as ring 142. Although embodiments are discussed herein with respect to ring 142, it will be appreciated that the wire tensioner tip 402a can be configured for use with any of the rings 102, 130, 142 and/or any other suitable ring of a circulator fixator 100.

Figure 8:
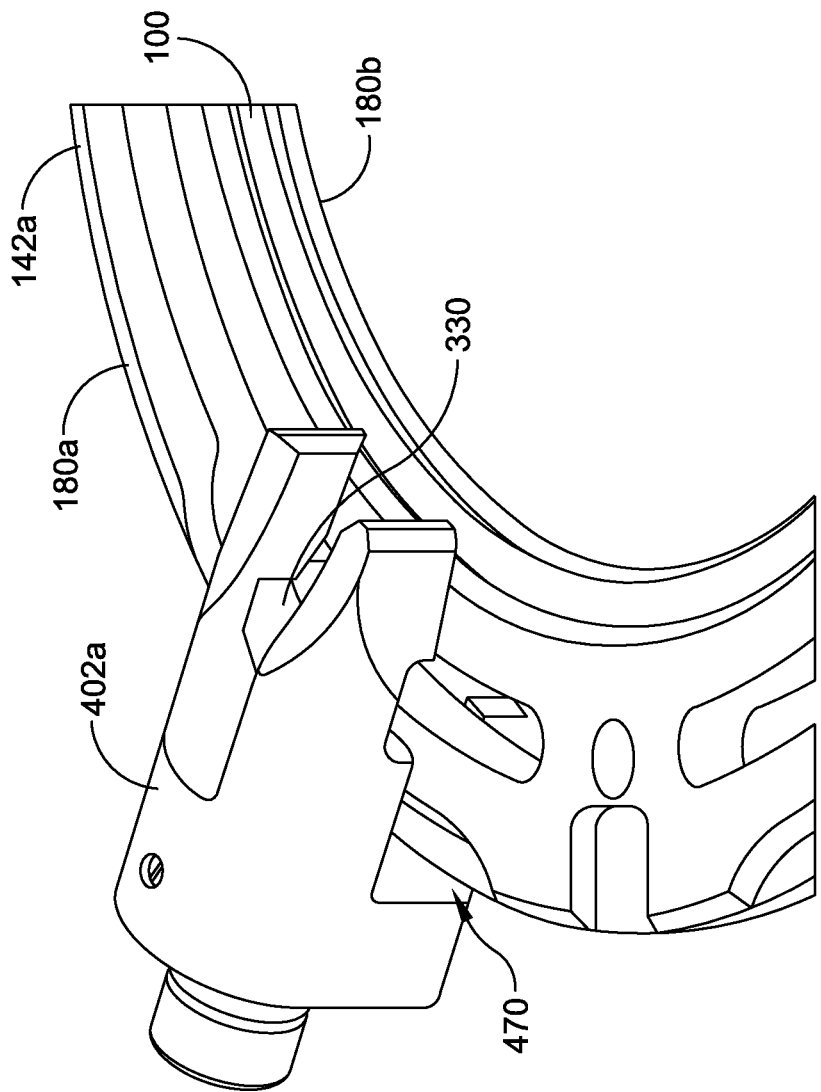
FIG. 8 is an isometric view of the wire tensioner tip of FIG. 7A coupled to a ring of a circular fixator in a straight engagement, in accordance with some embodiments.
Figure 9:
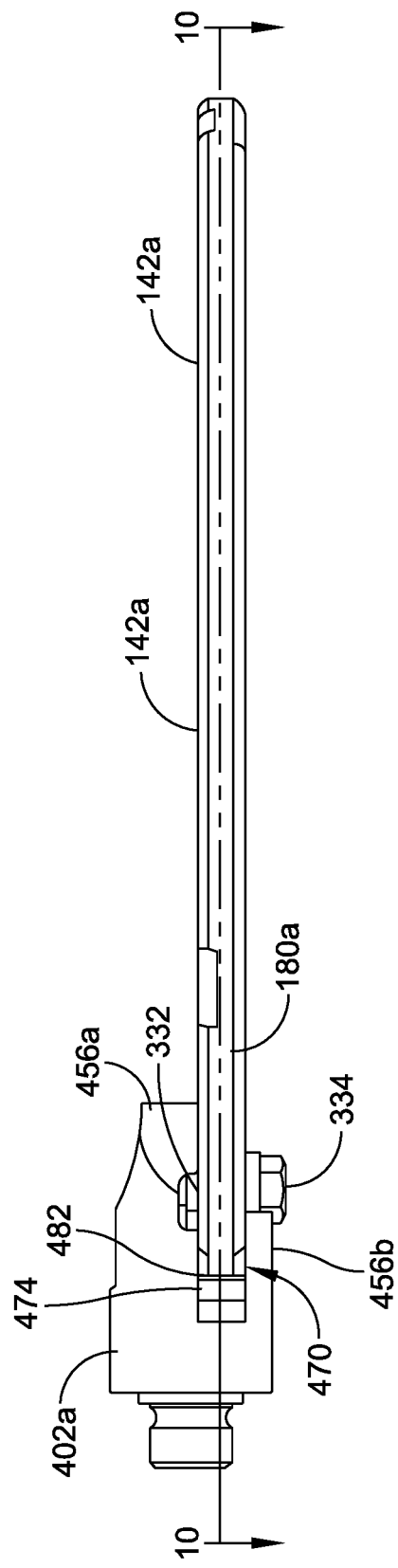
FIG. 9 is a side elevation view of the wire tensioner tip and ring of FIG. 8, in accordance with some embodiments.

The ring slot 470 is sized and configured to receive a ring of the circular fixator 100 therein, such as ring 142. The slot 470 can have a width equal to and/or greater than the thickness of the ring 142. In some embodiments, the first and second extensions 456a, 456b each have a length related to the width of the ring 142. For example, in some embodiments, the upper extension 456a has a length $X_1$ sufficient to extend from a first edge 180a of a ring 142a to a second edge 180b and the lower extension 456b has a length $X_2$ sufficient to extend from the first edge 180a of the ring 142a to a first side 182a of a slot 144 defined by the ring 142a (see FIG. 8). Although specific embodiments are discussed herein, it will be appreciated that the upper extension 456a and/or the lower extension 456b can define any suitable lengths $X_1$, $X_2$.

In some embodiments, the upper extension 456a defines a visualization cutout 460 extending from the outer surface 458a to the inner surface 458b. The visualization cutout 460 can be sized and configured to allow visualization of a fixation device 330, as described in greater detail below. The visualization cutout 460 is positioned within the upper extension 456a such that at least a portion of the visualization cutout 460 overlaps a slot 144 defined in the ring 142a when the ring 142a is inserted into the ring slot 470.

In some embodiments, a coupling extension 464 extends from the proximal surface 452 of the body 450. The coupling extension 464 includes a centrally located circular boss 466. The circular boss 466 and the body 402 define a continuous channel 468 extending therethrough substantially along a horizontal axis. The channel 468 is sized and configured to receive the wire 412 therethrough, as discussed in greater detail below. The coupling extension 464 is configured to couple the wire tensioner tip 402a to the wire tensioner 400. Although embodiments are discussed herein including a wire tensioner tip 402a having a coupling extension 464, it will be appreciated that the wire tensioner tip 402a can be coupled to the wire tensioner 400 using any suitable mechanism and/or can be formed integrally with the wire tensioner 400. Although embodiments are discussed herein including a wire tensioning tip 402a having a coupling extension 464 configured to be coupled to the wire tensioner 400, it will be appreciated that the coupling extension 464 can be positioned on and extend from the wire tensioner 400 and the wire tensioning tip 402a can include a cavity or other element configured to receive the coupling extension 464 therein.

In some embodiments, the wire tensioner tip 402a includes a pivoting engagement body 474 positioned between the first extension 456a and the second extension 456b. The pivoting engagement body 474 is positioned at least partially within the ring slot 470 and is configured to abut an edge (or outer surface) 180a of a ring 142a when the ring 142a is positioned within the ring slot 470. The pivoting engagement body 474 includes a body 476 defining a first hole 478 extending therethrough. The hole 478 is sized and configured to receive a pin 480 and/or other rotational coupling device therein.

A ring-facing surface 482 of the body 476 includes a plurality of projections 484 (e.g., teeth, diamond teeth, knurls, etc.) configured to abut an outer surface 180a of the ring 142a. The pivoting engagement body 474 is configured to pivot about the pin 480 such that the ring-facing surface 482 (and by extension the plurality of projections 484) can be aligned at an angle with respect to a horizontal axis of the wire tensioner tip 402a. For example, in some embodiments, the pivoting engagement body 474 can pivot a predetermined angle in one of a first and/or a second direction with respect to the horizontal axis of the wire tensioner tip 402. Although embodiments are discussed herein including a plurality of projections 484, it will be appreciated that similar performance may be provided by a textured and/or otherwise treated surface.

FIGS. 8-10B illustrate the wire tensioner tip 402a coupled to a ring 142a of a circular fixator 100 in a straight engagement, in accordance with some embodiments. The ring 142a is positioned within the ring slot 470 between the first extension 456a and the second extension 456b. An outer surface 180a of the ring 142a abuts a pivoting engagement body 474 (see FIG. 9). The wire tensioner tip 402a provides stabilization and counter-force when tensioning a wire 412 during a surgical procedure. In some embodiments, the first extension 456a is configured to extend over a bolt 332 of a fixation device 330. The first extension 456a can include a bolt cutout 484 extending from the inner surface 458b into the first extension 456a. The bolt cutout 484 is sized and configured to receive a head of the bolt 332 therein. In some embodiments, the inner surface 458b of the first extensions 456a is positioned above the bolt 332 when the wire tensioner tip 402a is coupled to the ring 142a.

The nut 334 of the fixation device 330 is configured to extend at least partially below the second extension 456b of the wire tensioner tip 402a such that the nut 334 can be tightened without removing the wire tensioner tip 402a. In some embodiments, the second extension 456b defines a cutout 486 sized and configured to receive a nut 334 and a socket (not shown) therein. Although embodiments are shown with the wire tensioner tip 402a in a specific orientation, it will be appreciated that the wire tensioner tip 402a can be rotated 180° prior to being coupled to the ring 142a such that the second extension 456b is positioned above the ring 142a and the first extension 456a is positioned below the ring 142a.

Figure 10A:
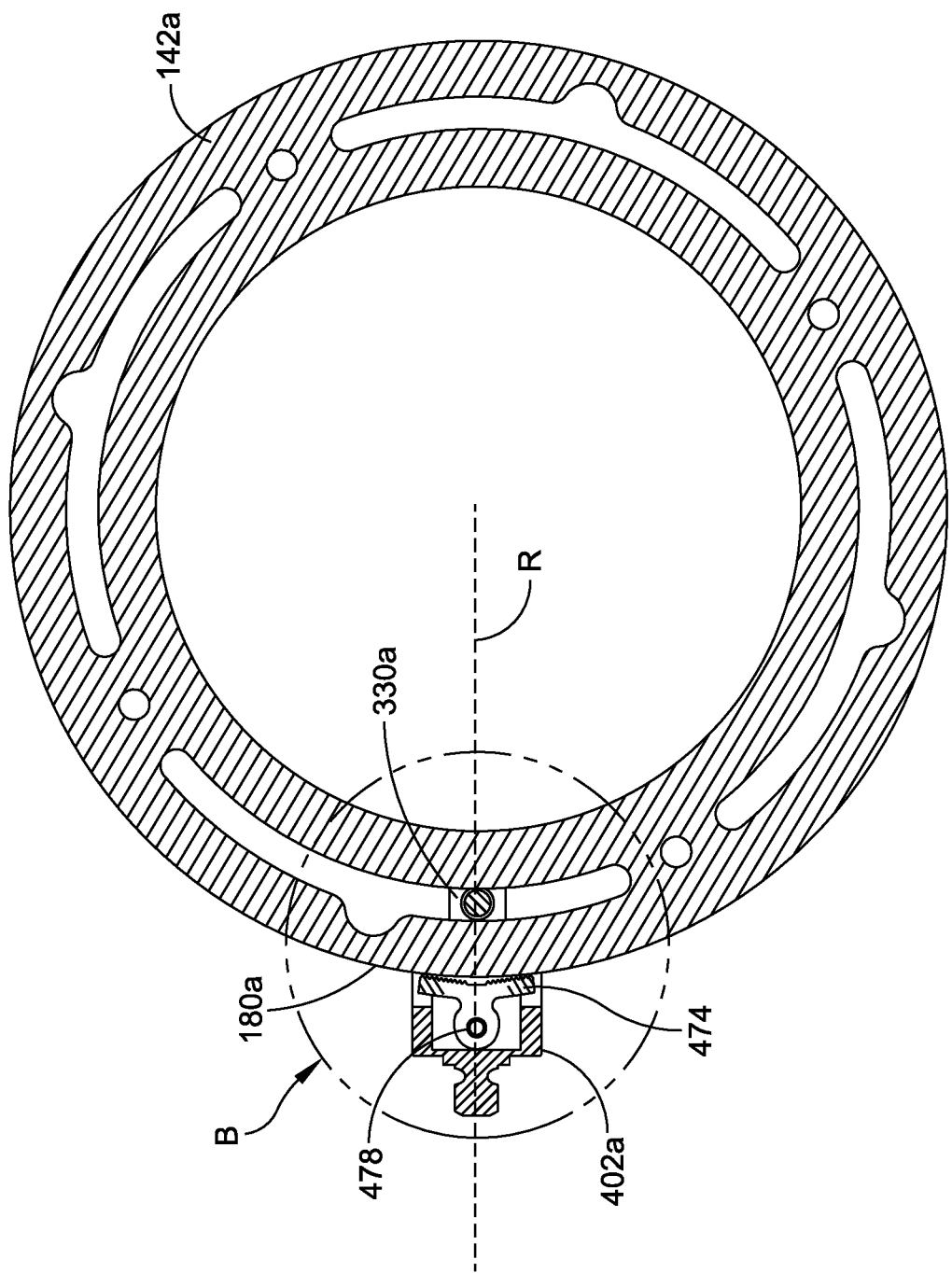
FIG. 10A is a cross-section of the wire tensioner tip and ring taken along line 10-10 in FIG. 9, in accordance with some embodiments.
Figure 10B:
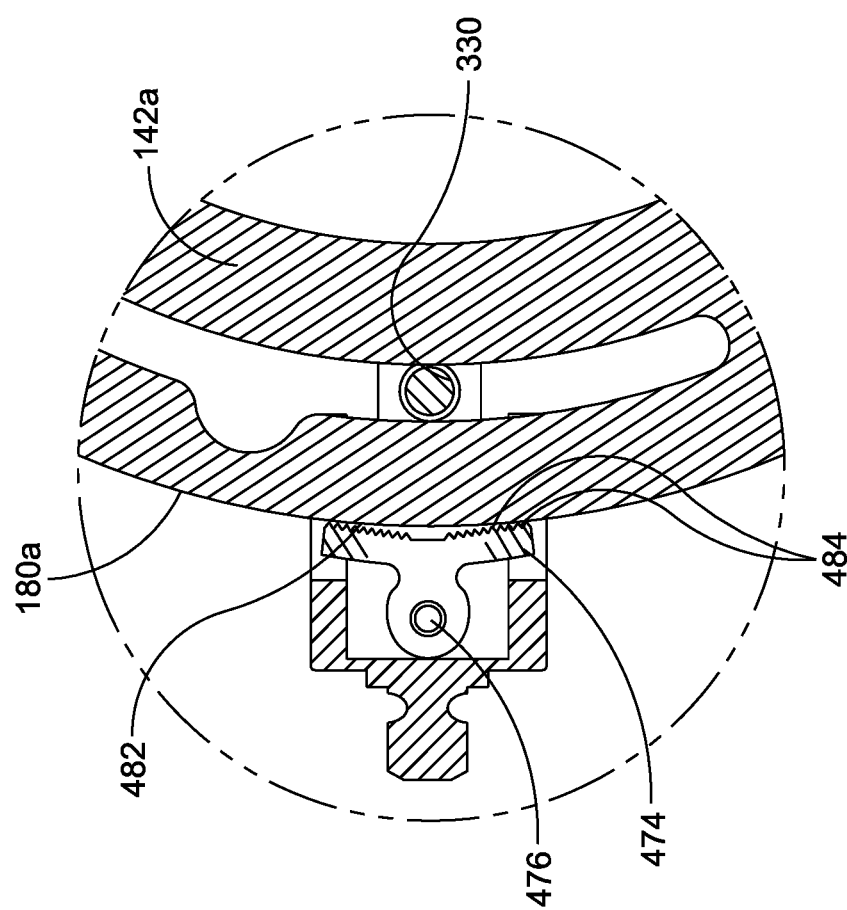
FIG. 10B is an expanded view of the area B of FIG. 10A, in accordance with some embodiments.
Figure 12:
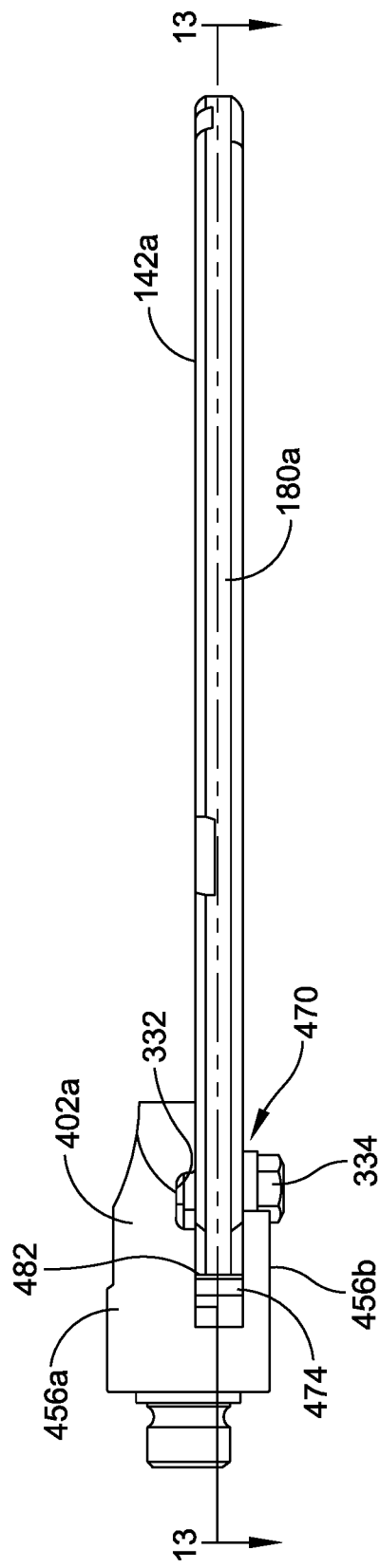
FIG. 12 is a side elevation view of the wire tensioner tip and ring of FIG. 11, in accordance with some embodiments.

As shown in FIG. 10A, the wire tensioner tip 402a is engaged with the ring 142a in a straight engagement such that the pivoting engagement body 474 is not-offset (i.e., is perpendicular with) a horizontal axis of the wire tensioner tip 402a. In addition, the horizontal axis of the wire tensioner tip 402a is aligned with a radius R of the ring 142a. As shown in FIG. 10B, the ring-facing surface 482 of the pivoting engagement body 474 is engaged with the outer surface 180a of the ring 142a. The plurality of teeth 484 create a frictional force with respect to the ring 142a and prevent movement (such as slippage, camming, etc.) of the wire tensioner 400 during tensioning of a wire 412.

Figure 13A:
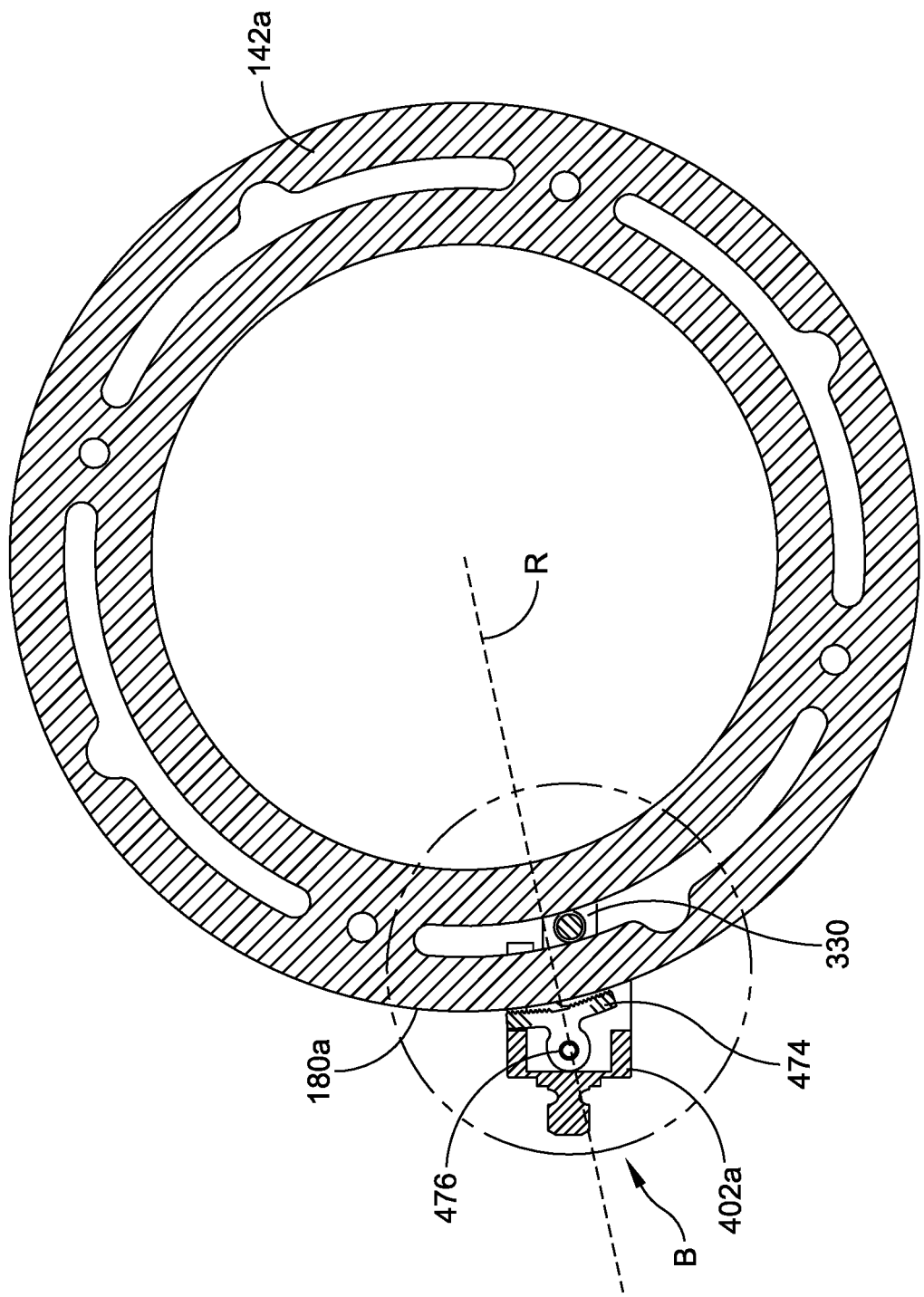
FIG. 13A is a cross-section of the wire tensioner tip and ring taken along line 13-13 in FIG. 12, in accordance with some embodiments.
Figure 13B:
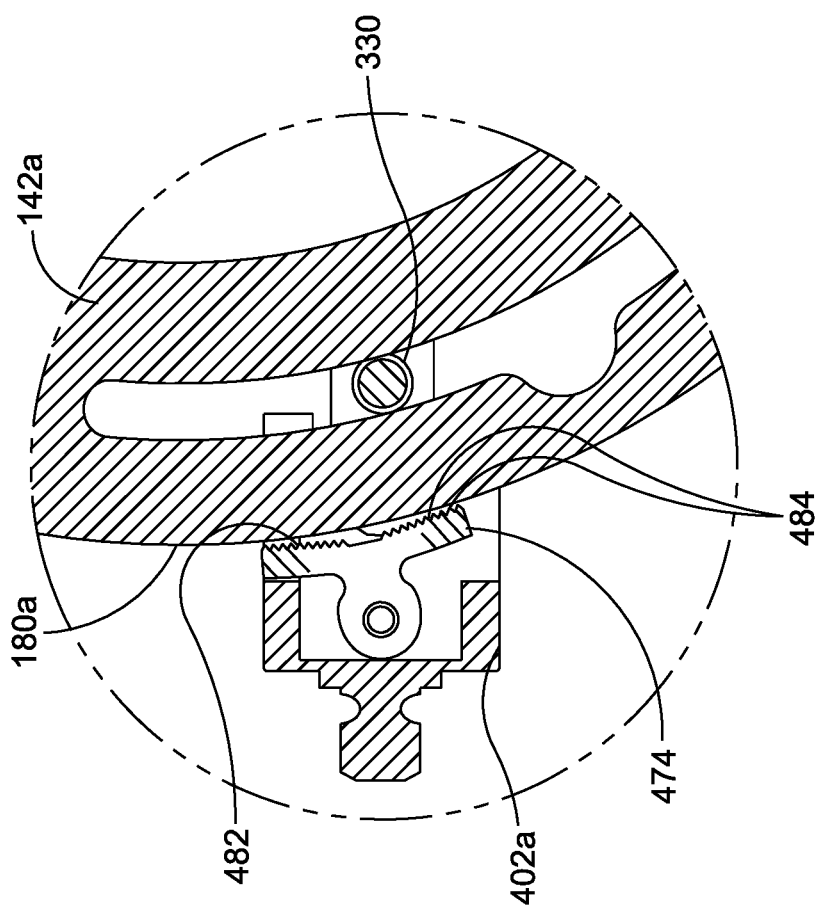
FIG. 13B is an expanded view of the area B of FIG. 13A, in accordance with some embodiments.
Figure 14A:
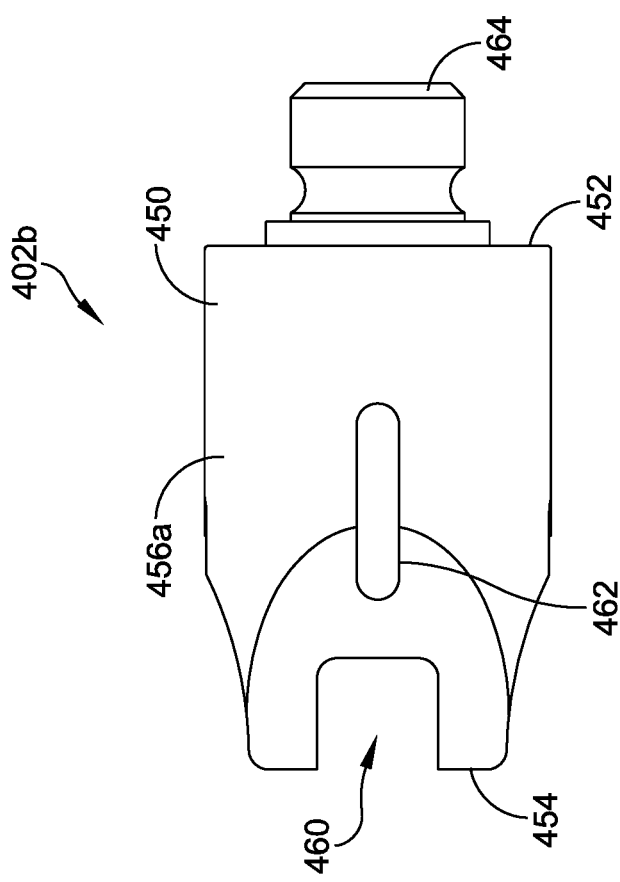
FIG. 14A is a plan view of a wire tensioner tip configured to be coupled to the wire tensioner of FIG. 6, in accordance with some embodiments.
Figure 14C:
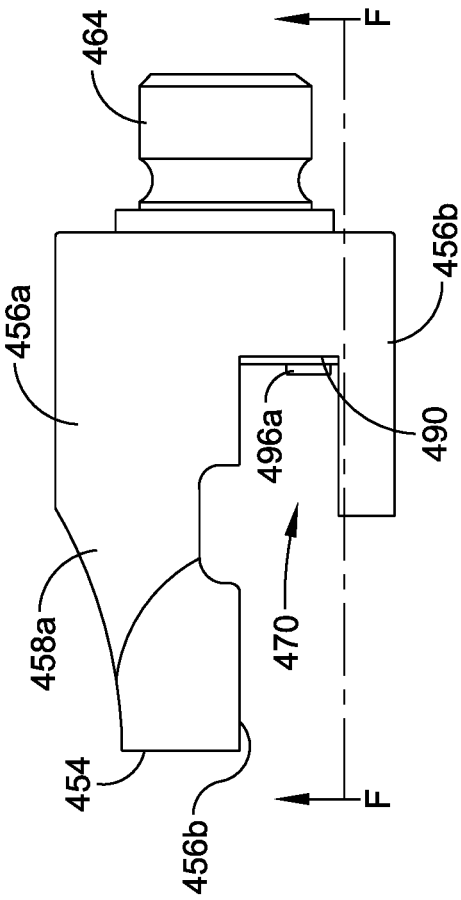
FIG. 14C is a side elevation view of the wire tensioner tip of FIG. 14A, in accordance with some embodiments.
Figure 14B:
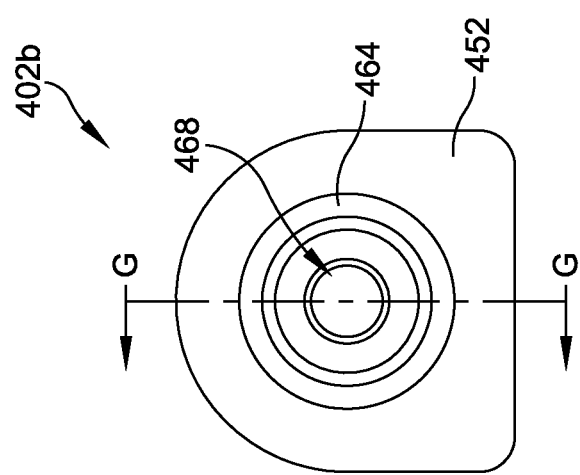
FIG. 14B is a posterior view of the wire tensioner tip of FIG. 14A, in accordance with some embodiments.
Figure 14E:
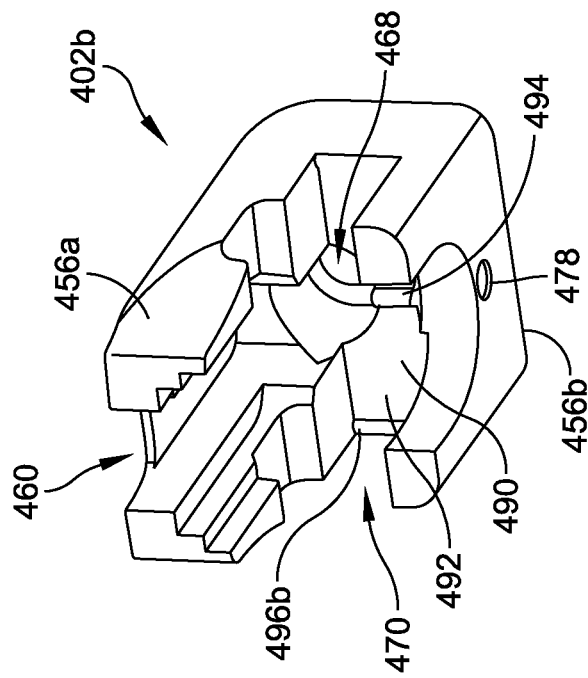
FIG. 14E is a front isometric view of the wire tensioner tip of FIG. 14A, in accordance with some embodiments.
Figure 14D:
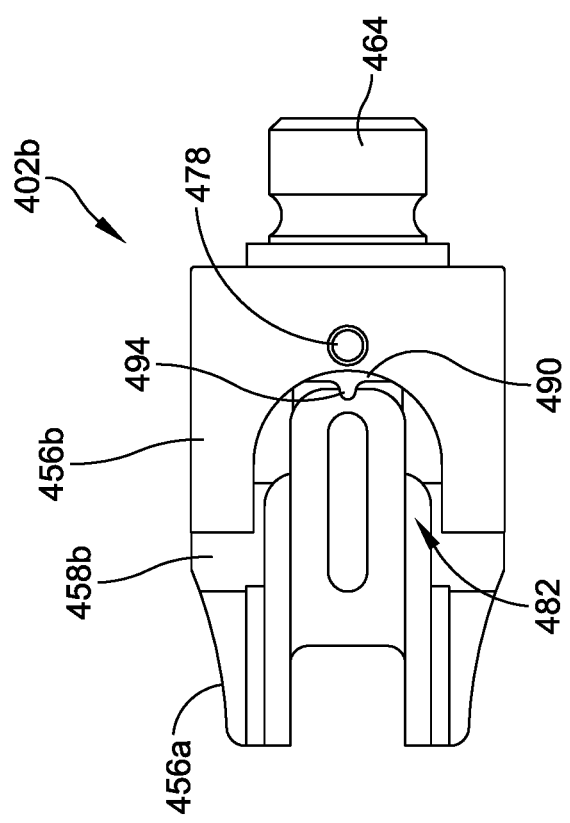
FIG. 14D is a bottom plan view of the wire tensioner tip of FIG. 14A, in accordance with some embodiments.

FIGS. 11-13B illustrate the wire tensioner tip 402a coupled to a ring 142a of a circular fixator 100 in an angled engagement, in accordance with some embodiments. The pivoting engagement body 474 is offset (i.e., at a non-perpendicular angle) with respect to the horizontal axis of the wire tensioner tip 402a. The horizontal axis of the wire tensioner tip 402a is also offset with respect to a radius of the ring 142a. As shown in FIG. 13B, the ring-facing surface 482a of the pivoting engagement body 474 is engaged with the outer surface 180a of the ring 142a. The pivoting engagement body 474 is offset from the body 450 of the wire tensioner tip 402a but maintains alignment and engagement with the outer surface 180a of the ring 142a. By maintaining alignment and engagement with the outer surface 180a, the pivoting engagement body 474 prevents movement of the wire tensioner 400 when in an offset (or angled) engagement.

FIGS. 14A-14G illustrate a wire tensioner tip 402b configured to be coupled to a wire tensioner 400, in accordance with some embodiments. The wire tensioner tip 402b is similar to the wire tensioner tip 402a discussed above in conjunction with FIGS. 7A-13B, and similar description is not repeated herein. The wire tensioner tip 402b includes a fixed engagement body 490 having a plurality of protrusions 494, 496a, 496b extending therefrom. The fixed engagement body 490 replaces the pivoting engagement body 474 of the wire tensioner tip 402a. The fixed engagement body 490 includes a generally rectangular body 492 defining a threaded hole 478 extending therethrough. The threaded hole 478 is configured to receive a ball plunger configured to couple to an additional and/or alternative tensioner tip extender (not shown).

The fixed engagement body 490 includes a central protrusion 494 extending from the rectangular body 492. The central protrusion 494 extends a predetermined distance into the ring slot 470. The central protrusion 494 is sized and configured to be received within a notch 186 defined by a first edge 180a of a ring 142b. The central protrusion 494 maintains the wire tensioner tip 402b when the wire tensioner tip 402 is engaged with the ring 142b in a straight engagement, as discussed in greater detail below.

In some embodiments, the fixed engagement body 490 includes a first side protrusion 496a and a second side protrusion 496b extending from the rectangular body 492. The first side protrusion 496a and the second side protrusion 496b can be symmetrically disposed at either end of the rectangular body 492. The first side protrusion 496a and the second side protrusion 496b extend a predetermined distance from rectangular body 492. In some embodiments, the first side protrusion 496a and the second side protrusion 496b each extend a length equal to the length of the center protrusion 494, although it will be appreciated that each of the center protrusion 494, the first side protrusion 496a, and/or the second side protrusion 496b can extend a greater and/or lesser length. The first side protrusion 496a and the second side protrusion 496b are sized and configured to be received within notches 186 defined by the first edge 180a of the ring 142b, as discussed in greater detail below with respect to FIG. 16B. In some embodiments, one or more of the protrusions 494, 496a, 496b can be omitted and/or additional protrusions can be added.

Figure 15:
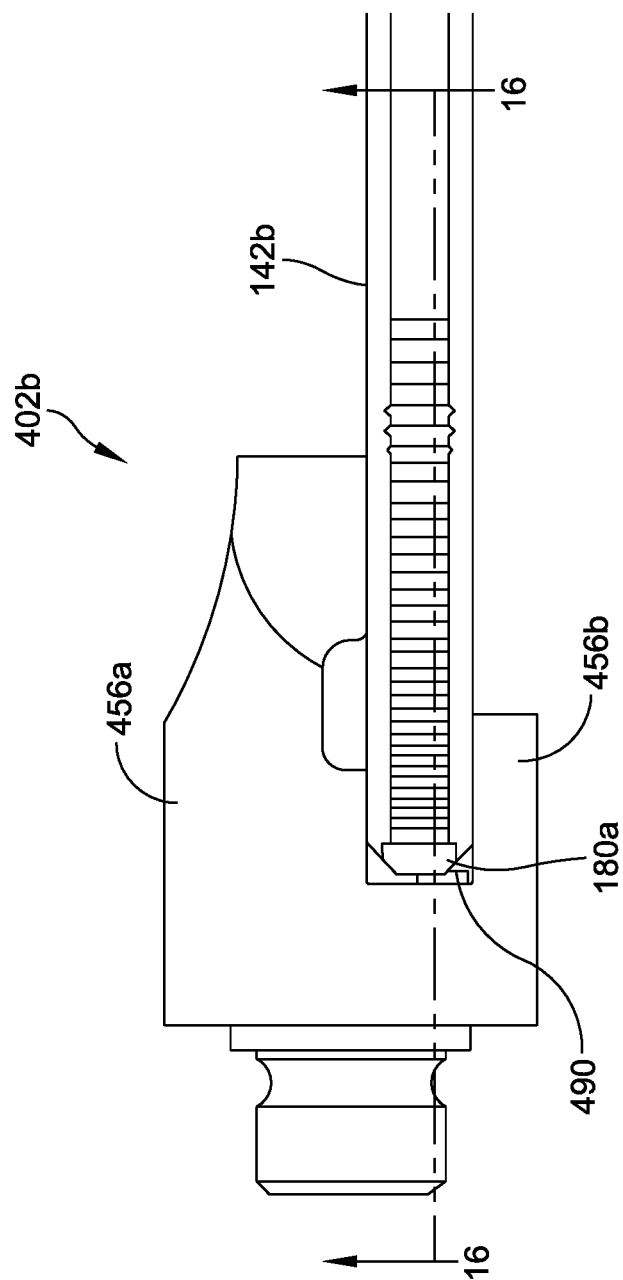
FIG. 15 is a side elevation view of the wire tensioner tip of FIG. 14A coupled to a ring of a circular fixator in a straight engagement, in accordance with some embodiments.
Figure 16A:
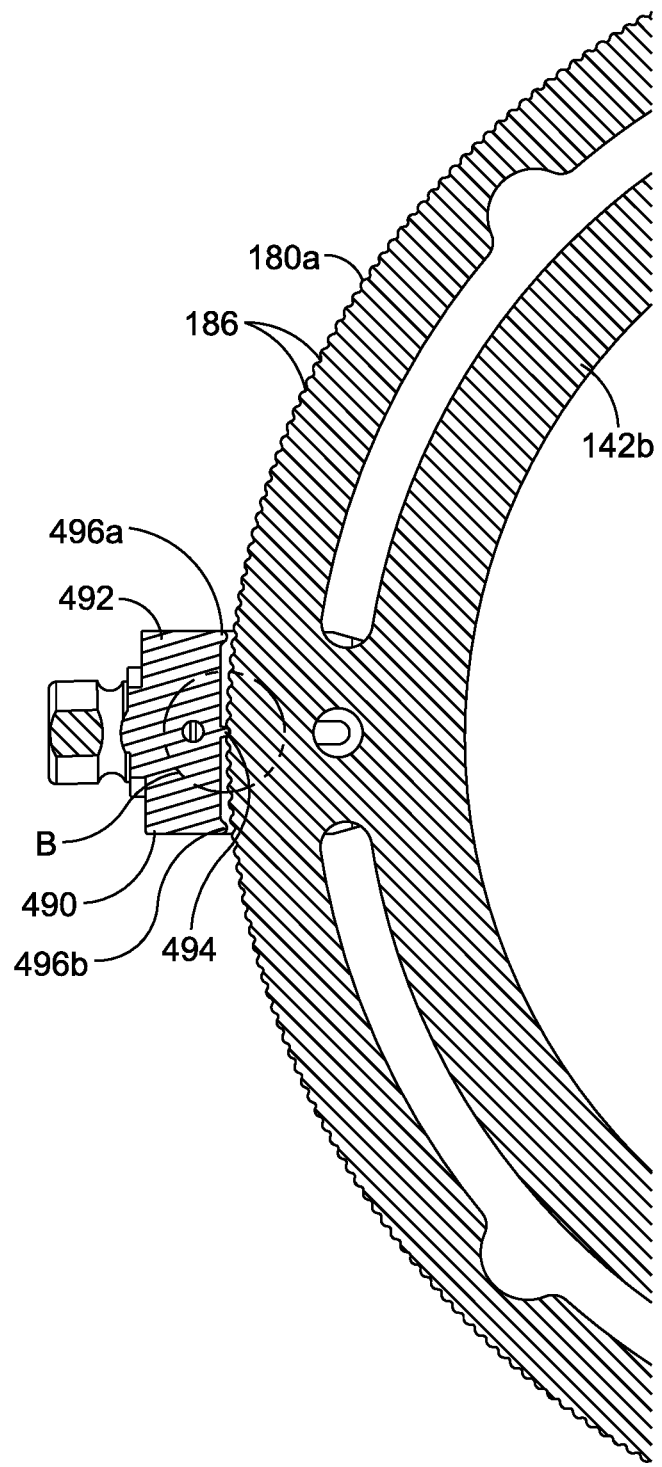
FIG. 16A is a cross-section of the wire tensioner tip and ring taken along line 16-16 in FIG. 15, in accordance with some embodiments.
Figure 16B:
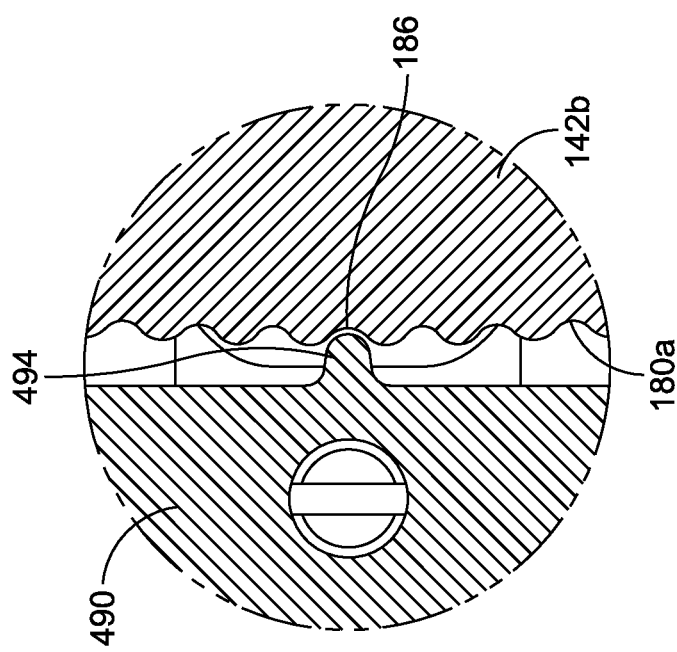
FIG. 16B is an expanded view of area B of FIG. 16A, in accordance with some embodiments.

FIGS. 15-16B illustrate the wire tensioner tip 402b coupled to a ring 142b in a straight engagement, in accordance with some embodiments. The ring 142b is at least partially inserted into the ring slot 470 the wire tensioner tip 402b. A first edge 180a of the ring 142b abuts the fixed engagement body 490. The outer edge 180a of the ring 142b defines a plurality of notches 186. The protrusions 494, 496a, 496b extending from the fixed engagement body 490 are sized and configured to be received within one of the plurality of notches 186. As shown in FIG. 16B, in a straight engagement, the central protrusion 494 is positioned within a notch 186. The central protrusion 494 and the notch 186 prevent movement (lateral movement, rotational movement, etc.) of the wire tensioner tip 402b during tensioning of a wire 412. The outer side protrusions 496a, 496b are not engaged with the ring 142b due to the curvature of the ring 142b.

Figure 17:
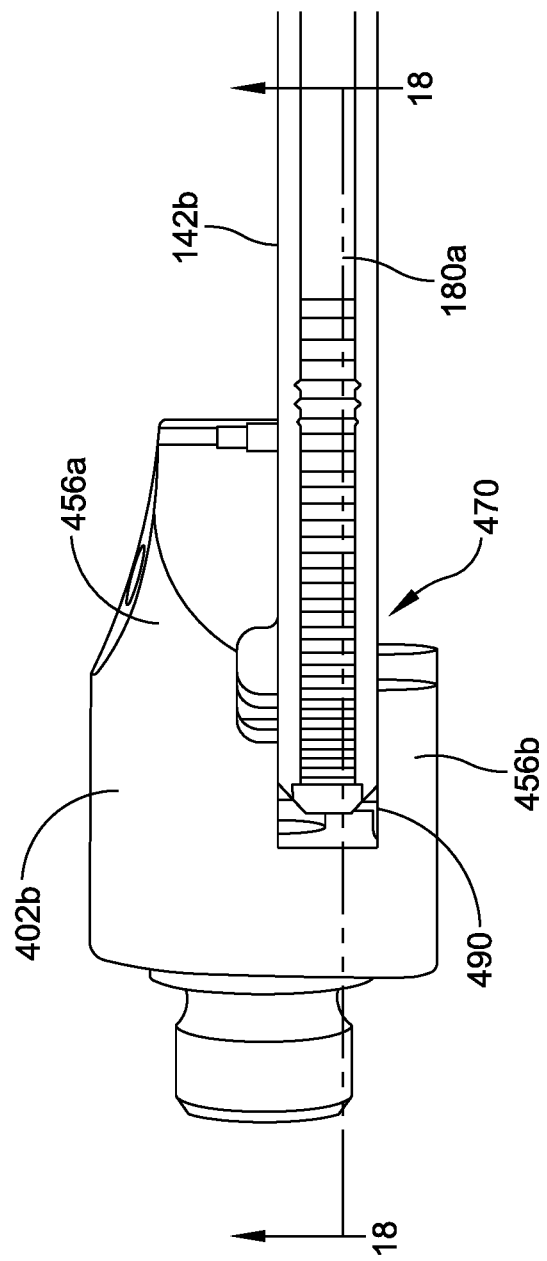
FIG. 17 is a side elevation view of the wire tensioner tip of FIG. 14A coupled to a ring of a circular fixator in an angled engagement, in accordance with some embodiments.
Figure 18A:
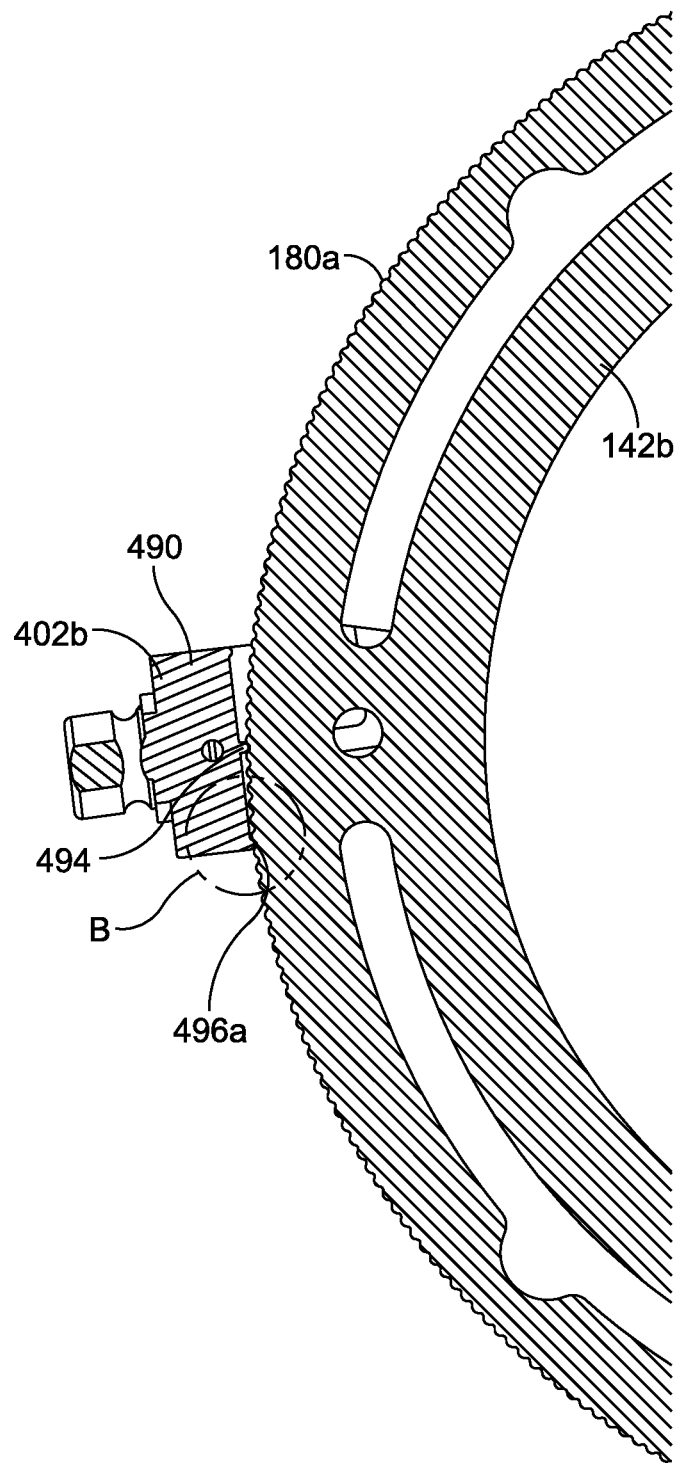
FIG. 18A is a cross-section of the wire tensioner tip and the ring taken along line 18-18 in FIG. 17, in accordance with some embodiments.
Figure 18B:
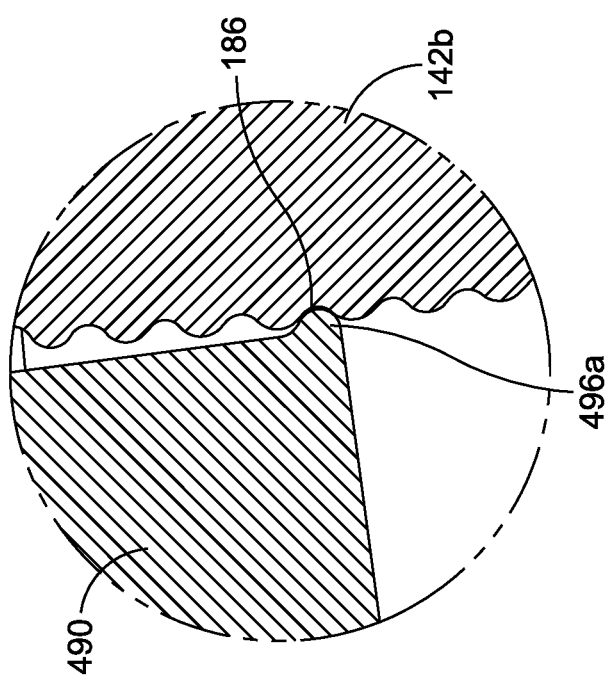
FIG. 18B is an expanded view of area B of FIG. 18A, in accordance with some embodiments.
Figure 19A:
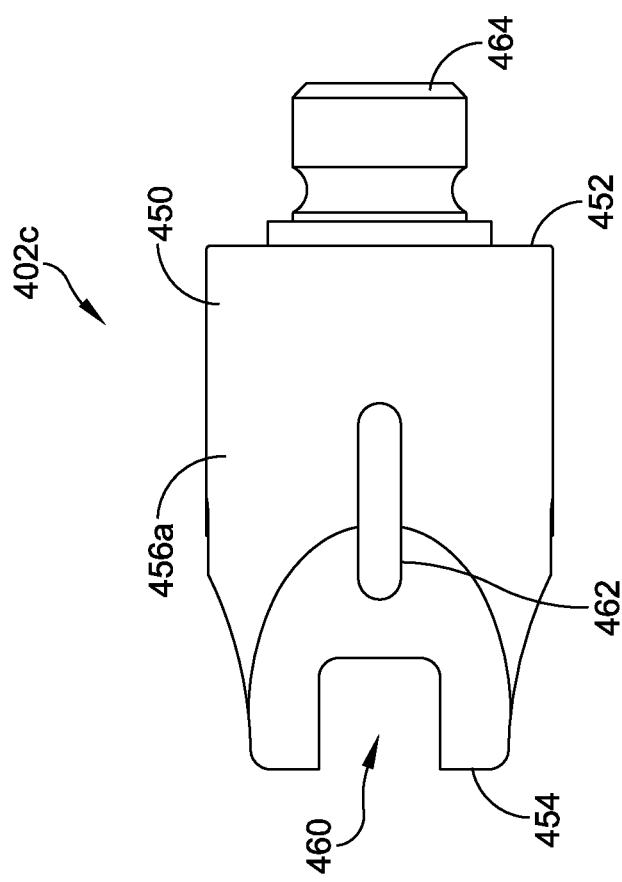
FIG. 19A is a plan view of a wire tensioner tip configured to be coupled to the wire tensioner of FIG. 6, in accordance with some embodiments.
Figure 19C:
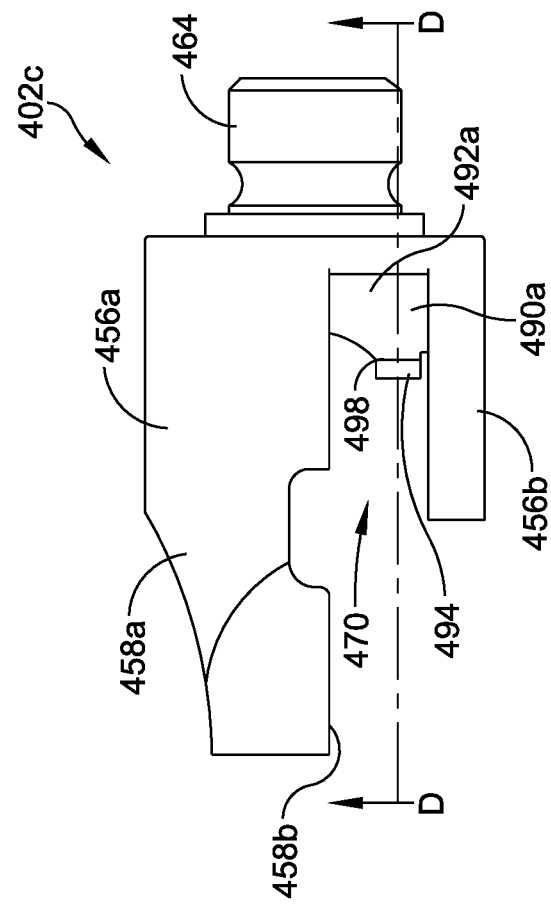
FIG. 19C is a side elevation view of the wire tensioner tip of FIG. 19A, in accordance with some embodiments.
Figure 19B:
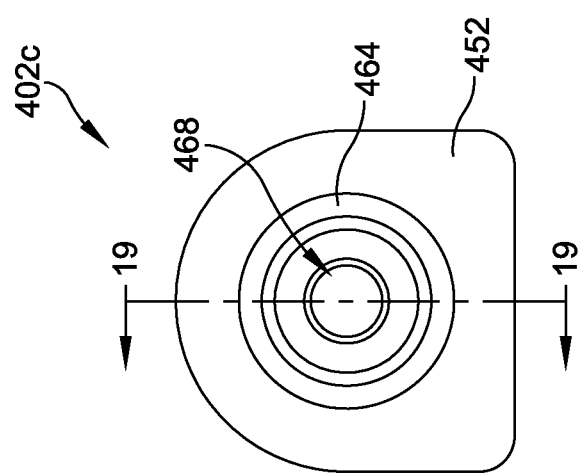
FIG. 19B is a posterior view of the wire tensioner tip of FIG. 19A, in accordance with some embodiments.
Figure 19E:
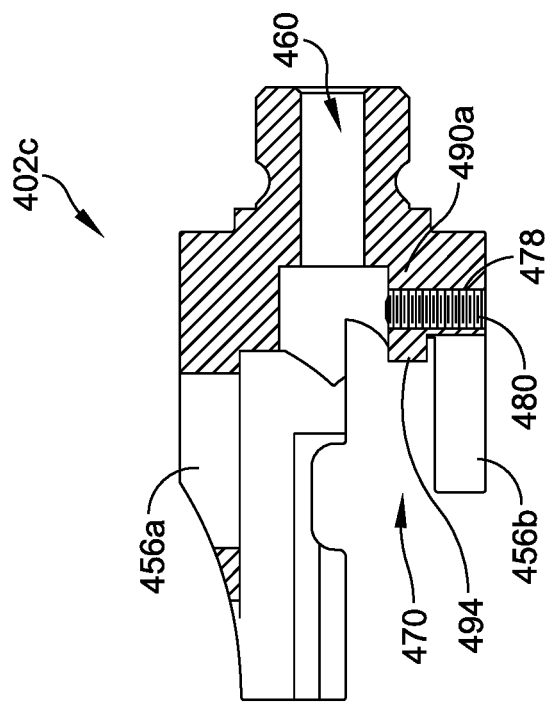
FIG. 19E is a cross-section of the wire tensioner tip taken along line E-E in FIG. 19B, in accordance with some embodiments.
Figure 19D:
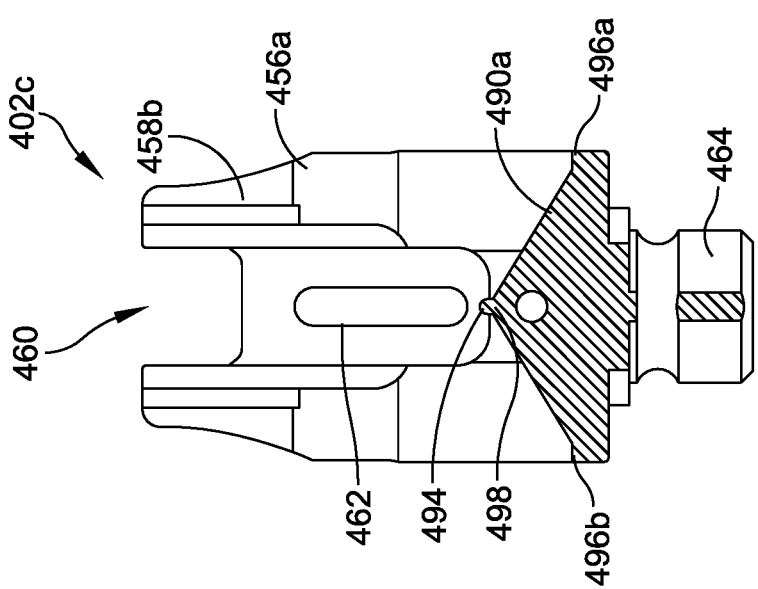
FIG. 19D is a cross-section of the wire tensioner tip taken along line D-D in FIG. 19C, in accordance with some embodiments.

FIGS. 17-18B illustrate the wire tensioner tip 402b coupled to the ring 142b in an angled engagement, in accordance with some embodiments. The horizontal axis of the wire tensioner tip 402b is offset with respect to a radius of the ring 142b. As shown in FIG. 18B, a first side protrusion 496a is engaged with a notch 186 defined in the first surface 180a of the ring 142b. The central protrusion 494 is also engaged with a notch 186. The first side protrusion 496a, the central protrusion 494, and the notch 186 prevent movement (lateral movement, rotational movement, etc.) of the wire tensioner tip 402b during tensioning of a wire 412.

FIGS. 19A-19E illustrate a wire tensioner tip 402c configured to be coupled to a wire tensioner 400, in accordance with some embodiments. The wire tensioner tip 402c is similar to the wire tensioner tip 402b discussed above in conjunction with FIGS. 14A-18B, and similar description is not repeated herein. The fixed engagement body 490a of the wire tensioner tip 402c includes a triangular body 492a having an apex 498 centrally positioned with respect to the wire tensioner tip 402c. A central protrusion 494 extends from the apex 498 of the triangular body 492a.

Figure 20:
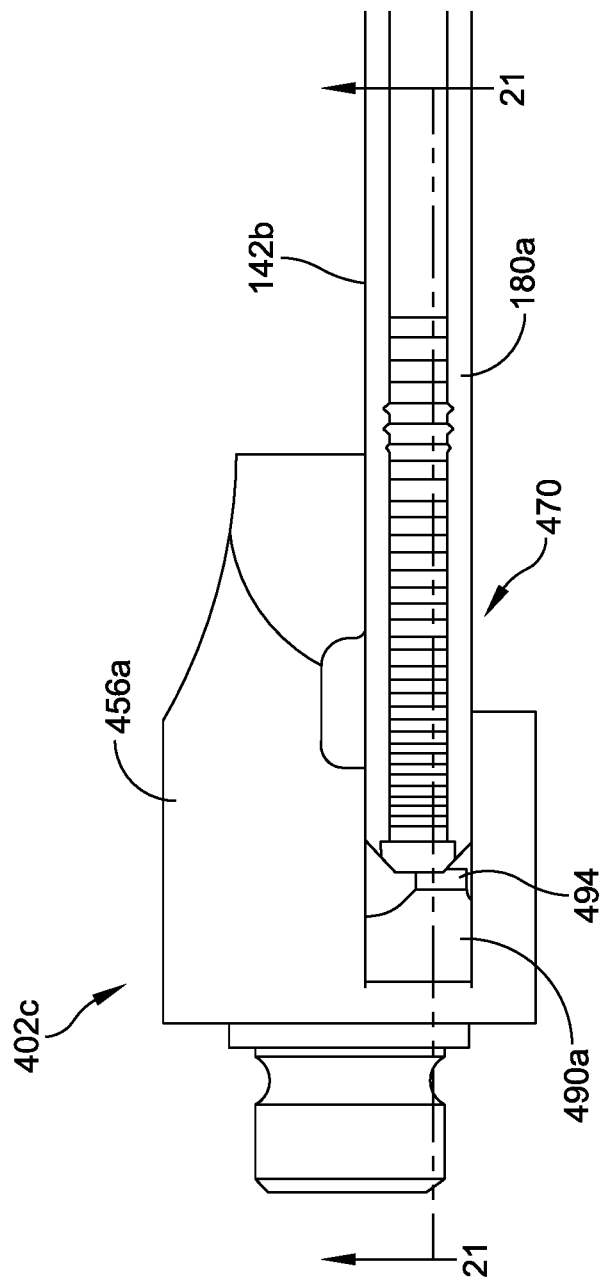
FIG. 20 is a side elevation view of the wire tensioner tip of FIG. 19A coupled to a ring of a circular fixator in a straight engagement, in accordance with some embodiments.
Figure 21A:
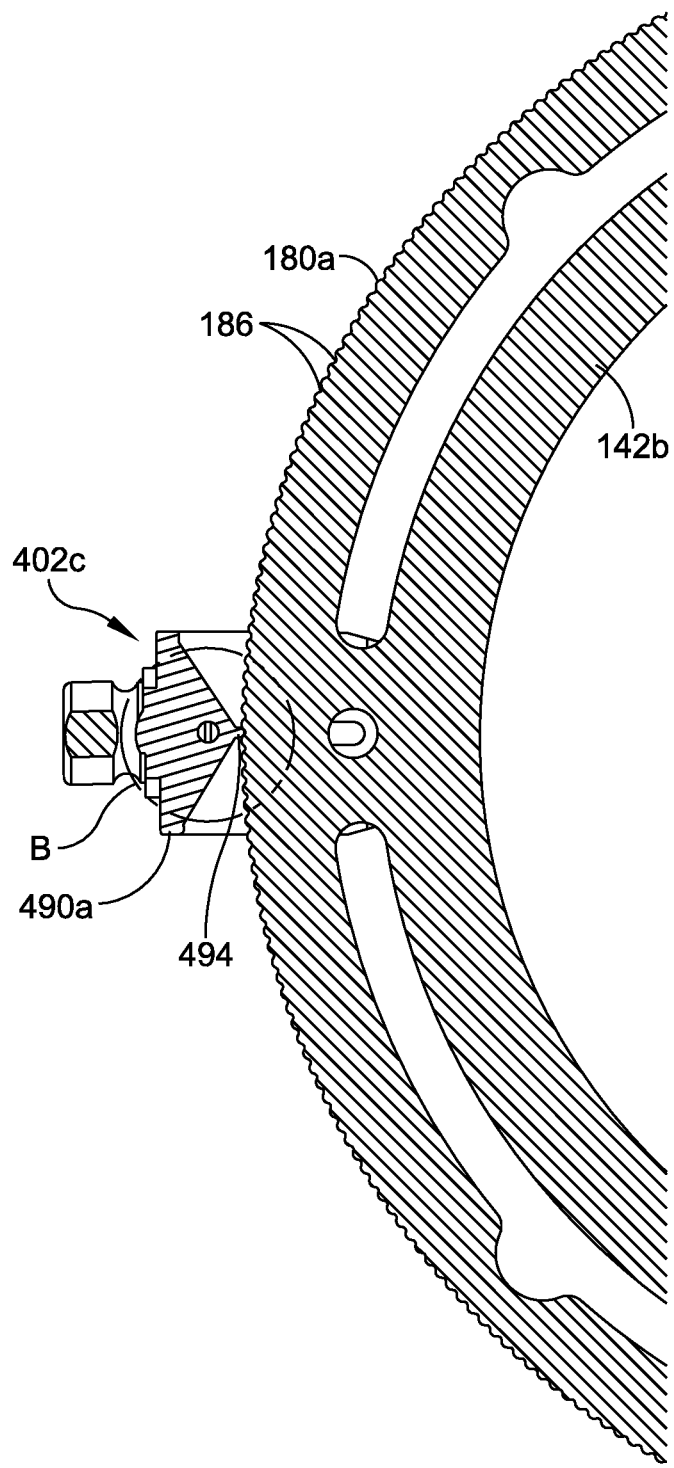
FIG. 21A is a cross-section of the wire tensioner tip and the ring taken along line 21-21 of FIG. 20, in accordance with some embodiments.
Figure 21B:
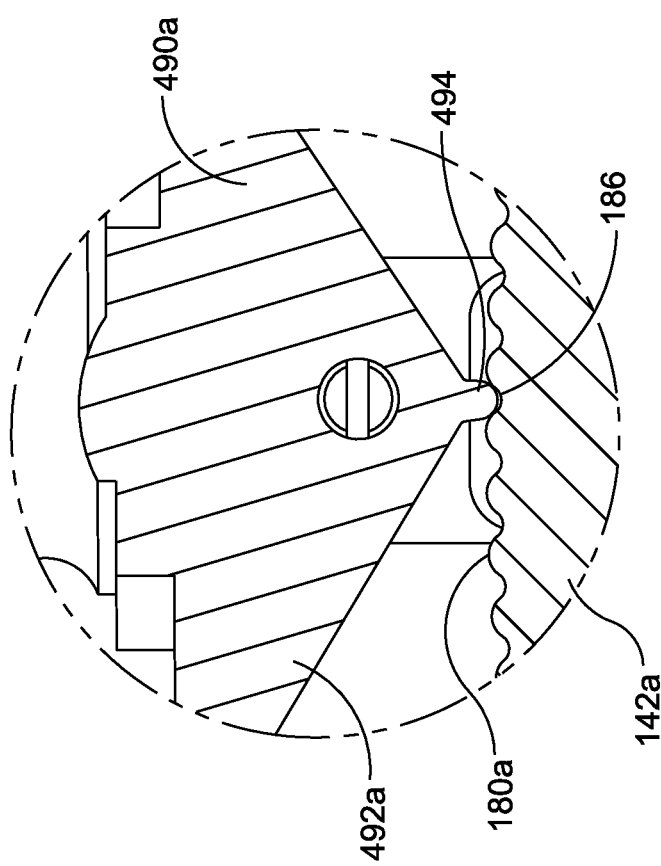
FIG. 21B is an expanded view of area B of FIG. 21A, in accordance with some embodiments.

FIGS. 20-21B illustrate the wire tensioner tip 402c coupled to a ring 142b in a straight engagement, in accordance with some embodiments. The ring 142b is at least partially inserted into the ring slot 470 the wire tensioner tip 402c. As shown in FIG. 21B, in a straight engagement, the central protrusion 494 is positioned within a notch 186. The central protrusion 494 and the notch 186 prevent movement (lateral movement, rotational movement, etc.) of the wire tensioner tip 402c during tensioning of a wire 412. The outer side protrusions 496a, 496b are not engaged with the ring 142b in a straight engagement.

Figure 22:
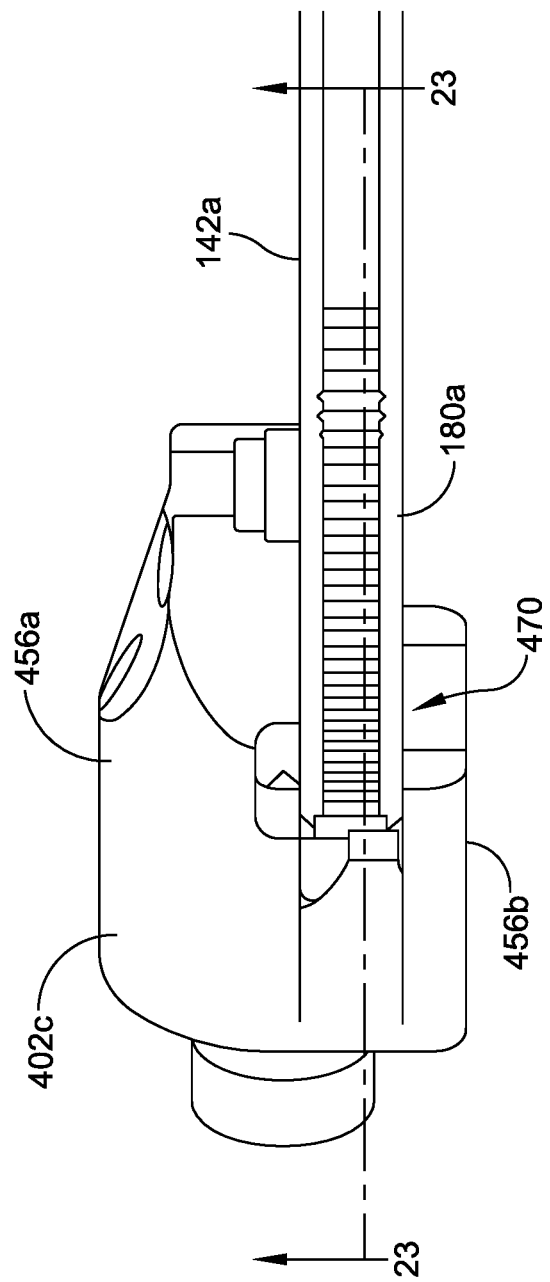
FIG. 22 is a side elevation view of the wire tensioner tip of FIG. 19A coupled to a ring of a circular fixator in an angled engagement, in accordance with some embodiments.
Figure 23A:
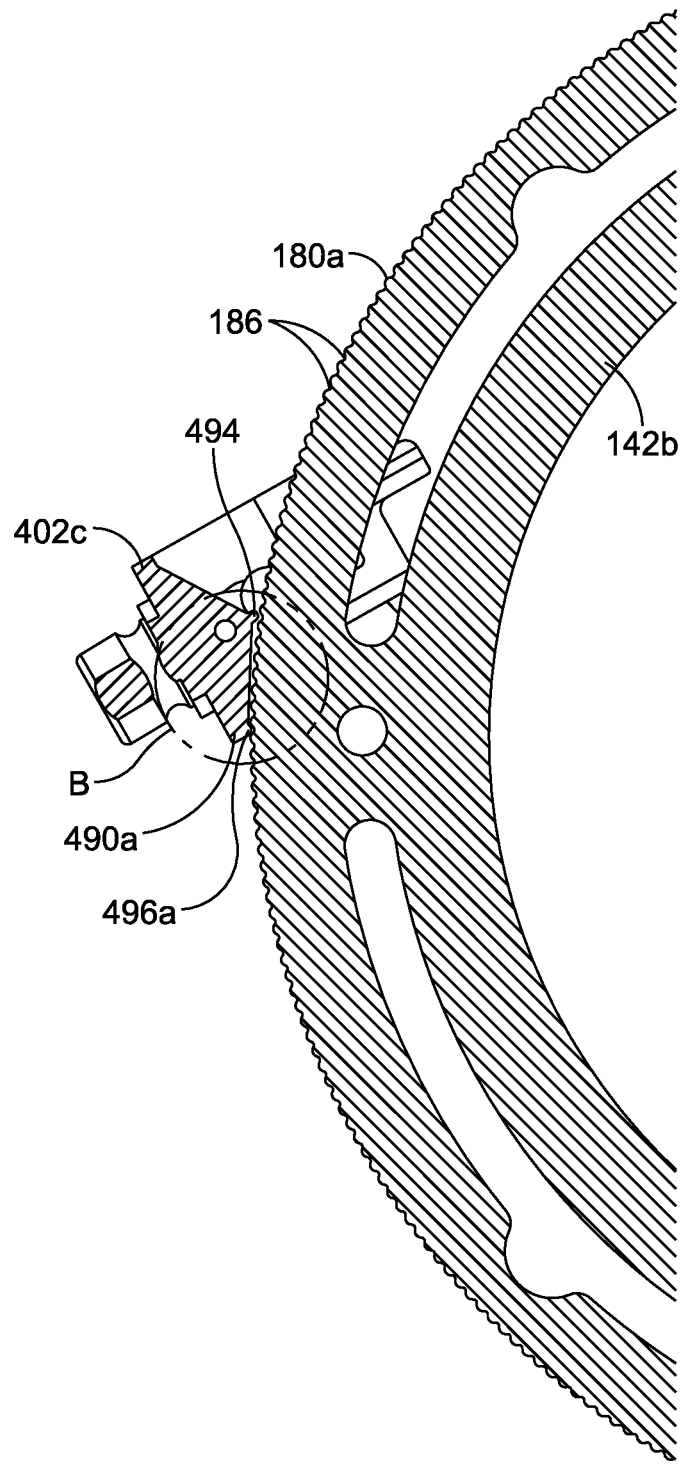
FIG. 23A is a cross-section of the wire tensioner tip and the ring taken along line 23-23 in FIG. 22, in accordance with some embodiments.
Figure 23B:
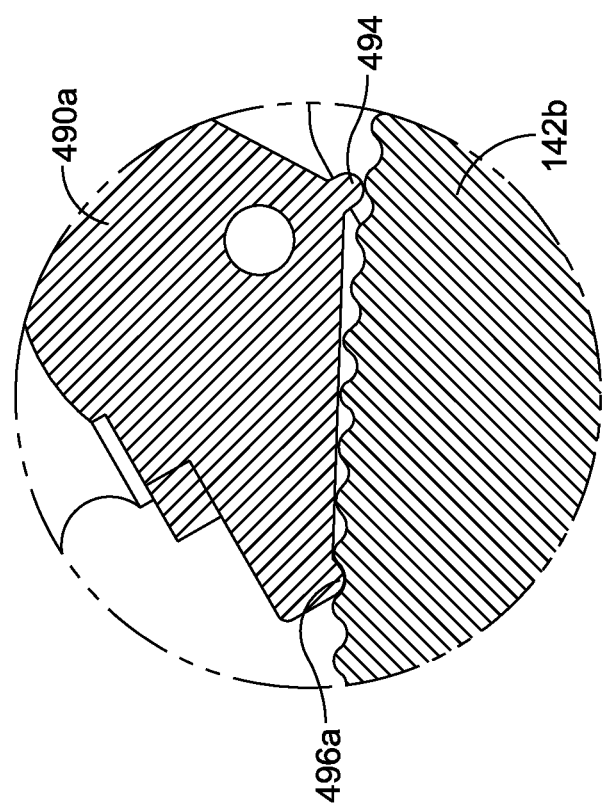
FIG. 23B is an expanded view of area B of FIG. 23A, in accordance with some embodiments.

FIGS. 22-23B illustrate the wire tensioner tip 402c coupled to the ring 142b in an angled engagement, in accordance with some embodiments. The horizontal axis of the wire tensioner tip 402c and the fixed engagement body 490a are offset with respect to a radius of the ring 142b. As shown in FIG. 23B, a first side protrusion 496a is engaged with a notch 186 defined in the first surface 180a of the ring 142b. The first side protrusion 496a and the notch 186 prevent movement (lateral movement, rotational movement, etc.) of the wire tensioner tip 402b during tensioning of a wire 412. The central protrusion 494 is not engaged with a notch, although it will be appreciated that the central protrusion 494 can be partially engaged with a notch when the angle between the horizontal axis of the wire tensioner tip 402c and the radius of the ring 142a is reduced.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A wire tensioner tip, comprising:
    a body having a first extension and a second extension spaced apart to define a ring slot;
    a substantially triangular engagement body disposed within the ring slot, wherein the engagement body is fixed with respect to the body and includes one or more projections configured to engage an outer surface of a ring positioned within the ring receiving slot; and
    a coupling element extending from the body and configured to couple the body to a wire tensioner.

2. The wire tensioner tip of claim 1, wherein the engagement body is configured to pivot with respect to the body.

3. The wire tensioner tip of claim 1, wherein the one or more projections comprise a plurality of teeth extending from a surface of the engagement body.

4. The wire tensioner tip of claim 3 wherein the engagement body has a substantially rectangular shape.

5. The wire tensioner tip of claim 3 wherein the engagement body includes a first side projection extending from a first end of the engagement body and a second side projection extending from a second end of the engagement body.

6. The wire tensioner tip of claim 1 wherein the engagement body includes a central projection extending from a center of the engagement body.

7. The wire tensioner tip of claim 1, wherein the body and the coupling element define a wire receiving channel extending therethrough.

8. The wire tensioner tip of claim 7, wherein the wire receiving channel is aligned with a horizontal axis of the body.

9. The wire tensioner tip of claim 1, wherein the first extension defines a slot extending from a first end into the first extension.

10. The wire tensioner tip of claim 1, wherein the first extension has a first length and the second extension has a second length less than the first length.

11. The wire tensioner tip of claim 1, wherein the coupling element comprises a boss.

12. A wire tensioner, comprising:
    a tensioning body comprising a handle portion and a tensioner, wherein the handle portion includes a first handle and a second handle configured to actuate the tensioner, and wherein the tensioner is configured to apply a force to a wire inserted into the tensioner; and
    a tensioner tip coupled to the tensioning body, comprising:
        a tip body having a first extension and a second extension spaced apart to define a ring slot;
        a substantially rectangular engagement body disposed within the ring slot, wherein the engagement body is fixed with respect to the body and includes one or more projections configured to engage an outer surface of a ring positioned within the ring receiving slot.

13. The wire tensioner of claim 12, wherein the tensioner tip is removable from the tensioner.

14. The wire tensioner of claim 12, wherein the engagement body is configured to pivot with respect to the tip body.

15. The wire tensioner of claim 12, wherein the tensioner tip and the tensioner define a channel sized and configured to receive a wire therethrough.

16. A system, comprising:
   a circular fixator comprising at least one ring defining a slot;
   a wire fixation element sized and configured to be positioned within the slot of the circular fixator; and
   a wire tensioner comprising:
      a tensioning body comprising a handle portion and a tensioner, wherein the handle portion includes a first handle and a second handle configured to actuate the tensioner, and wherein the tensioner is configured to apply a force to a wire inserted into the tensioner; and
      a tensioner tip coupled to the tensioning body, comprising:
         a tip body having a first extension and a second extension spaced apart to define a ring slot sized and configured to receive the at least one ring;
         a substantially triangular engagement body disposed within the slot, wherein the engagement body is fixed with respect to the body and includes one or more projections configured to engage an outer surface of the at least one ring when the at least one ring is positioned within the ring slot.

17. The system of claim 16, wherein the tensioner tip is removable from the tensioning body.

18. A method, comprising:
   coupling a wire to a first fastener and a second fastener, wherein the wire extends through at least a first bone, and wherein each of the first fastener and the second fastener are coupled to a ring of a circular fixator;
   tightening the first fastener to lock a first end of the wire in a fixed position;
   coupling a wire tensioner to a second end of the wire, wherein the wire tensioner comprises:
      a tensioning body including a tensioner defining a channel sized and configured to receive the wire therethrough; and
      a tensioner tip coupled to the tensioning body, comprising:
         a tip body having a first extension and a second extension spaced apart to define a ring slot sized and configured to receive the ring therein;
         a substantially triangular engagement body disposed within the slot, wherein the engagement body is fixed with respect to the body and includes one or more projections configured to engage an outer surface of the ring when the ring is positioned within the ring slot;
   tensioning the wire, wherein the tensioner is configured to apply a tensioning force to the wire; and
   tightening the second fastener to lock the second end of the wire in a fixed position.

* * * * *